(12) United States Patent
Medin et al.

(10) Patent No.: US 8,445,635 B2
(45) Date of Patent: May 21, 2013

(54) MODIFIED H2 RELAXIN FOR TUMOR SUPPRESSION

(75) Inventors: Jeffrey A Medin, North York (CA); Joshua Daniel Silvertown, Toronto (CA); Alastair J. S. Summerlee, Guelph (CA)

(73) Assignee: Armour Therapeutics Inc., Toronto, Ontario (CA)

( * ) Notice: Subject to any disclaimer, the term of this patent is extended or adjusted under 35 U.S.C. 154(b) by 803 days.

(21) Appl. No.: 12/664,824

(22) PCT Filed: Apr. 11, 2007

(86) PCT No.: PCT/CA2007/000604
§ 371 (c)(1),
(2), (4) Date: Dec. 15, 2009

(87) PCT Pub. No.: WO2007/115414
PCT Pub. Date: Oct. 18, 2007

(65) Prior Publication Data
US 2010/0286046 A1 Nov. 11, 2010

Related U.S. Application Data
(60) Provisional application No. 60/790,788, filed on Apr. 11, 2006.

(51) Int. Cl.
*C07K 14/00* (2006.01)
(52) U.S. Cl.
USPC .......................... 530/324; 514/19.3; 514/19.4
(58) Field of Classification Search
USPC ................................. 530/324; 514/19.3, 19.4
See application file for complete search history.

(56) References Cited

U.S. PATENT DOCUMENTS

| 4,835,251 | A | 5/1989 | Burnier et al. |
|---|---|---|---|
| 5,053,488 | A | 10/1991 | Hudson et al. |
| 5,179,195 | A | 1/1993 | Hudson et al. |
| 5,320,953 | A | 6/1994 | Hudson et al. |
| 5,326,694 | A | 7/1994 | Hudson et al. |
| 5,464,756 | A | 11/1995 | Henner et al. |
| 6,200,953 | B1 | 3/2001 | Schwabe et al. |
| 7,833,526 | B2 | 11/2010 | Amento et al. |
| 2011/0059108 | A1* | 3/2011 | Amento et al. ............ 424/158.1 |

FOREIGN PATENT DOCUMENTS
CA 2425712 A1 4/2002

OTHER PUBLICATIONS

Bullesbach, Erika E., Schwabe, Christian, "The Relaxin Receptor-binding Site Geometry Suggests a Novel Gripping Mode of Interaction", The Journal of Biological Chemistry, vol. 275, No. 45, Issue of Nov. 10, pp. 35276-35280, 2000.
Bullesbach, Erika, E., Yang, Su, Schwabe, Christian, "The Receptor-binding Site of Human Relaxin II", The Journal of Biological Chemistry, vol. 267, No. 32, Issue of Nov. 15, pp. 22957-22960, 1992.
Bathgate Ross A.D., Samuel,Chrishan S., Burazin, Tanya C.D., Gundlach, Andrew L., Tregear Geoffrey W., "Relaxin: new peptides, receptors and novel actions", TRENDS in Endocrinology and Metabolism, vol., 14, No. 5, pp. 207-213, Jul. 2003.
Bathgate, Ross A., Ivell, Richard, Sanborn, Barbara M., Sherwood, O. David, Summers, Roger J., "Receptors for Relaxin Family Peptides", Ann. N.Y. Acad. Sci. 1041: 61-76 (2005).
Fei, David T.W., Gross, Mary C., Lofgren, Julie L., Mora-Worms, Marina, Chen, Anthony B., "Cyclic Amp Response to Recombinant Human Relaxin by Cultured Human Endometrial Cells—A Specific and High Throughput In Vitro Bioassay", Biochemical and Biophysical Research Communications, vol. 170, No. 1, 1990, Jul. 16, 1990, pp. 214-222.
Gunnersen, J.M., Roche, P.J., Tregear, G.W., Crawford, R.J., "Characterization of human relaxin gene regulation in the relaxin-expressing human prostate adenocarcinoma cell line LNCaP.FGC", Journal of Molecular Endocrinology, 1995, 15, 153-166.
Hsu, Sheau Yu, et al., "Activiation of Orphan Receptors, by the Hormone Relaxin", Science, 295, 671-674 (2002).
Hudson, P., Haley, J., John, M., Cronk, M., Crawford, R., Haralambidis, J. Tregear, J., Shine, J., Niall, H., "Structure of a genomic clone encoding biologicall active human relaxin", Nature, vol. 301, Feb. 17, 1983, pp. 628-631.
Silvertown, J.D. et al., "Analog of H2 relaxin exhibits antagonistic properties and impairs prostate tumor growth", FASEB J. Mar. 2007, vol. 21, No. 3, pp. 754-765, ISSN: 0892-6638.
Naldini, Luigi, Blomer, Ulrike, Gallay, Philippe, Ory, Daniel, Mulligan, Richard, Gage, Fred H., Verma, Inder M., Trono, Didier, "In Vivo Gene Delivery and Stable Transduction of Nondividing Cells by a Lentiviral Vector", Science, New Series, vol. 272, No. 5259 (Apr. 12, 1996), pp. 263-267.
Parsell, Dawn A., Mak, John Y., Amento, Edward P., Unemori, Elaine N., "Relaxin Binds to and Elicits a Response from Cells of the Human Monocyctic Cell Line, THP-1*", The Journal of Biological Chemistry, vol. 271, No. 44, Issue of Nov. 1, pp. 27936-27941, 1996.
Scott, D.J., Tregear, G.W., Bathgate, R.A.D., "LGR7-Truncate Is a Splice Variant of the Relaxin Receptor LGR7 and Is a Relaxin Antagonist in Vitro", Ann. N.Y. Acad. Sci., 1041: 22-26 (2005).
Sherwood, David O., "Relaxin's Physiological Roles and Other Diverse Actions", Endocrine Reviews 25(2): 205-234 (2004).
Silvertown, Josh D., NG, Jonathan, Sato, Takeya, Summerlee, Alastair J., Medin, Jeffery A., "H2 relaxin overexpression increases in vivo prostate xenograft tumor growth and angiogenesis", Int. J. Cancer: 118, 62-73 (2006).
Silvertown Josh D., Geddes, Brad J., Summerlee, Alastair J.S., "Adenovirus-Mediated Expression of Human Prorelaxin Promotes the Invasive Potential of Canine Mammary Cancer Cells", Endocrinology 2003 144:3683-3691.
Silvertown, Josh D., Summerlee, Alastair J.S., Klonisch, Thomas, "Relaxin-Like Peptides in Cancer", Int. J. Cancer: 107, 513-519 (2003).

(Continued)

*Primary Examiner* — David Lukton
(74) *Attorney, Agent, or Firm* — Bereskin & Parr LLP/S.E.N.C.R.L., s.r.l.; Melanie Szweras

(57) ABSTRACT

Modified H2 relaxms which act as antagonists of the relaxm receptor in cells and tissues, in particular, modified H2 relaxms comprising one or more alterations of the ammo acid sequence at positions B 13, B17 and B20 located in the receptor binding domain The antagonists retain affinity to the receptor, but do not substantially activate the receptor once bound thereto The H2 relaxm antagonists are used in compositions and methods for the treatment of cancers wherein a relaxm receptor is expressed.

35 Claims, 8 Drawing Sheets

OTHER PUBLICATIONS

Silvertown, Josh D., Fraser, Russell, Poterski, Roman S., Geddes, Brad, Summerlee, Alastair J.S., "Central Effects of Long-Term Relaxin Expression in the Rat", Ann. N.Y. Acad. Sci., 1041: 216-222 (2005).

Tashima L.S., Mazoujian, G., Bryant-Greenwood, G.D., "Human relaxins in normal, benign and neoplastic breast tissue", Journal of Molecular Endocrinology (1994) 12, 351-364.

Zhao, Ling, Roche, Peter J., Gunnersen, Jenny M., Hammond Vicki E., Tregear, Geoffrey W., Wintour, Marelyn, Beck, Felix, "Mice without a Functional Relaxin Gene Are Unable to Deliver Milk to Their Pups", Endocrinology, vol. 140: 445-453, 1999.

Nachman, Ronald J., Roberts, Victoria A., Holman, G. Mark, Beier, Ross C., "Pseudodipeptide analogs of the pyrokinin/PBAN (FXPRLa) insect neuropeptide family containing carbocyclic Pro-mimetic conformational components", Regulatory Peptides 57 (1995) 359-370.

* cited by examiner

US 8,445,635 B2

MODIFIED H2 RELAXIN FOR TUMOR SUPPRESSION

This application is a National Stage of International Application No. PCT/CA2007/000604, filed Apr. 11, 2007, which claims the benefit of U.S. Provisional Application No. 60/790,788, filed Apr. 11, 2006, the contents of which are herein incorporated by reference.

FIELD OF THE INVENTION

The invention relates to modified forms of H2 relaxin. More specifically, the invention is directed to modified forms of H2 relaxin that are antagonists of the relaxin receptor and have use in various compositions and methods for the treatment of cancers.

BACKGROUND OF THE INVENTION

Throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure in their entirety.

Also, throughout this application various nonstandard abbreviations are used as follows: H2 relaxin (relaxin-2); ΔH2 (mutated/modified H2 relaxin); rH2 (recombinant H2 relaxin); RBD (receptor binding domain); LRR (leucine rich region); LV (lentiviral vector); UHN (University Health Network); eGFP (enhanced GFP); PMH (Princess Margaret Hospital); BLI (bioluminescence imaging); and CM (conditioned medium).

Humans possess three distinct genes for relaxin, termed relaxin-1 (H1), relaxin 2 (H2) and relaxin-3 (H3). All insulin and relaxin-like peptides share a homologous molecular structure that define them as members of the insulin-like superfamily. Each mature peptide (~6-7 kDa) consists of an A and B chain joined by two interchain disulfide bonds, and one intrachain disulfide bond contained in the A chain (Sherwood, O D. (2004). Relaxins physiological roles and other diverse actions. Endocr Rev. 25:205-34).

Relaxin is classically known as a reproductive hormone with peak levels circulating during pregnancy (Sherwood, O D. (2004). Relaxins physiological roles and other diverse actions. Endocr Rev. 25:205-34). However, studies have broadened the scope for relaxin biology and it is now considered a pleiotropic hormone with functions in the cardiovascular and central nervous systems, neovascularization, and as an agent involved in ECM and connective tissue remodeling believed to be mediated by matrix metalloproteinases (MMPs) (Bani, D. 1997. Relaxin: a plelotropic hormone. Gen Pharmacol. 28:13-22; Bathgate, R. A., Samuel, C. S., Burazin, T. C., Gundlach, A. L., Tregear, G. W. 2003. Relaxin: new peptides, receptors and novel actions. Trends Endocrinol Metab. 14:207-1 3). Due to its several functions, relaxin has been the focus of research for a variety of uses. PCT/US01/42484 describes methods of modulating apoptosis by the use of relaxin agonists or antagonists. PCT/AU2004/000798 describes cyclic peptide analogues of the relaxin superfamily proteins where such peptides may be used for treating hyperplastic or neoplastic disorders. Further, the overexpression of H2 relaxin from PC-3 prostate xenograft tumors has been demonstrated to exhibit increased growth compared to controls (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118:62-73).

Peptides of the relaxin family have a conserved receptor binding domain (RBD) located on the B-chain (Sherwood, O D. (2004). Relaxins physiological roles and other diverse actions. Endocr Rev. 25:205-34). All H1, H2, H3 hormones and their orthologues sequenced to date have the Arg-X-X-X-Arg-X-X-Ile motif at positions B13, B17 and B20, with the exception of porcine relaxin (H2 equivalent in human) which has a valine residue at B20 (Sherwood, O D. (2004). Relaxins physiological roles and other diverse actions. Endocr Rev. 25:205 34). Studies have confirmed that this RBD motif is essential for relaxin biological activity and high-affinity receptor binding (Bullesbach, E. E., Schwabe, C. 2000. The relaxin receptor-binding site geometry suggests a novel gripping mode of interaction. J Biol. Chem. 275:35276-80; Bullesbach, E. E., Yang, S., Schwabe, C. 1992. The receptor-binding site of human relaxin H. A dual prong-binding mechanism. J Biol. Chem. 267:22957-60). H2 relaxin derivatives have been synthesized with the B13 and B17 arginines replaced with other amino acid residues (Bullesbach, E. E., Yang, S., Schwabe, C. 1992. The receptor-binding site of human relaxin II. A dual prong binding mechanism. J Biol. Chem. 267:22957-60). In particular, a dilysine H2 relaxin (at sites B13, B17) was synthesized that was rendered biologically inactive, however, it retained about a 2200-fold lower affinity for receptor binding than the level of wild type H2 relaxin. Further, studies demonstrated that substitution of the isoleucine residue at B20 with alanine reduced receptor binding by 3 orders of magnitude (Bullesbach, E. E., Schwabe, C. 2000. The relaxin receptor-binding site geometry suggests a novel gripping mode of interaction. J Biol. Chem. 275:35276-80).

To date, no effective relaxin peptide antagonists have been described in the literature. The LGR7 relaxin receptor has been exploited as a potential antagonist to neutralize relaxin activity. Soluble LGR7 ectodomains were demonstrated to bind relaxin and inhibit receptor mediated signaling of cAMP and suppress nipple development in mice (Hsu, S. Y., Nakabayashi, K., Nishi, S., Kumagai, J., Kudo, M., Sherwood, O D., Hsueh, A. J. 2002. Activation of orphan receptors by the hormone relaxin. Science. 295:671-74). Additionally, a truncated LGR7 splice variant was reported to abrogate relaxin LGR7 binding in vitro (Scott D. J., Tregear, G. W., Bathgate, R A. 2005. LGR7 truncate is a splice variant of the relaxin receptor LGR7 and is a relaxin antagonist in vitro. Ann NY Acad Sci. 1041:22-C).

While studies have demonstrated the importance of the RBD sequence for relaxin binding, there has not previously been demonstrated any modified (mutant/altered) H2 relaxin that binds to the receptor with high affinity and effectively acts as an antagonist of the receptor. Also, a modified relaxin H2 antagonist has never previously been developed that binds to the receptor and is involved in tumor suppression. Lastly, the ΔH2 relaxin antagonist described in the present invention essentially blocks relaxin signaling the receptor presented on the cell surface instead of neutralizing circulating hormone.

SUMMARY OF THE INVENTION

The present invention is directed to the identification and production and use of modified H2 relaxin as an antagonist for clinical use in compositions and methods for the treatment of cancers in tissues expressing the relaxin receptor. The relaxin antagonists of the invention have one or more modifications to the relaxin binding domain (RBD) that does not substantially alter its binding to the receptor, i.e. the modified relaxins bind with high affinity to the receptor but that does not substantially activate the receptor.

Cells stimulated with recombinant relaxin antagonists result in impaired cAMP signaling in in vitro studies. Expression or over-expression of modified forms of H2 relaxin (denoted herein as 'ΔH2') is demonstrated to antagonize the receptor in a manner that suppresses prostate xenograft tumor growth. Mutation of the receptor binding domain renders ΔH2 essentially non-stimulatory as determined by measurement of cAMP levels. In a competitive assay, ΔH2 exhibited antagonistic activity by blocking recombinant H2 relaxin from binding to relaxin receptors on THP-1 cells. When PC-3 cell lines were engineered to over-express eGFP, wild-type H2, or ΔH2 and implanted into NOD/SCID mice, tumor xenografts overexpressing ΔH2 relaxin displayed smaller tumor volumes compare to H2 and eGFP control tumors. Zymographic analyses, plasma osmolality readings, and CD31 staining suggest that ΔH2 also modulates physiological parameters in vivo. Animals harboring PC-3 tumors overexpressing wild-type H2 exhibited greater incidences of metastasis compared to mice of the ΔH2 and eGFP groups. Intratumoral injections of lentivectors engineered to express ΔH2/eGFP led to suppressed PC-3 tumor growth compared to wild-type H2 or eGFP LV-infected groups.

Taken together, the present invention demonstrates a clinical role for H2 relaxin antagonists in tumor growth. As such, it is now demonstrated for the first time that modification of the H2 relaxin confers the hormone derivative with antagonistic properties, offering a novel treatment for cancers.

According to an aspect of the invention there is provided a modified H2 relaxin having one or more modifications in the RBD region. The modified relaxin acts as an antagonist of the relaxin receptor.

The modified H2 relaxin of the invention can be used in a variety of in vitro, in vivo or ex vivo applications and methods.

According to another aspect of the invention there is provided a modified H2 relaxin having one or more amino acid modifications in the B-chain, wherein said modified H2 relaxin binds with substantially high affinity to the relaxin receptor and is an effective antagonist of the relaxin receptor in cells and tissues.

According to another aspect of the invention there is provided a modified H2 relaxin having one or more mutations of the B13 to B20 positions of the receptor binding domain (RBD) wherein such modified relaxin functions as an antagonist of the receptor.

According to another aspect of the invention there is provided a modified H2 relaxin having one or more mutations of B13, B17 and B20 of the receptor binding domain (RBD) wherein such modified relaxin functions as an antagonist of the receptor.

According to another aspect of the invention there is provided a modified H2 relaxin having one or more modifications in the Arg-X-X-X-Arg-X-X-Ile motif of the receptor binding domain (RBD). The modified H2 relaxin functioning as an antagonist of the relaxin receptor.

According to another aspect of the invention there is provided a modified H2 relaxin having a double lysine mutation in the receptor binding domain (RBD).

According to another aspect of the invention there is provided a modified H2 relaxin having a lysine substitution at the B13 and B17 positions of the receptor binding domain (RBD).

According to yet a further aspect of the invention there is provided a modified H2 relaxin antagonist which binds to the relaxin receptor with high affinity and with substantially no activation of the receptor The invention also relates to nucleic acids encoding the H2 relaxin antagonists of the invention, expression vectors containing the nucleic acid molecules, host cells containing the nucleic acid molecules and compositions of such antagonists and nucleic acids encoding therefore.

According to another aspect of the present invention is a method for treating cancers in a subject, the method comprising administering to said subject in need thereof, a therapeutically effective amount of a H2 relaxin antagonist having a modification in the receptor binding domain (RBD).

According to an aspect of the invention is a method for treating cancer in a subject, the method comprising administering to said subject in need thereof, a therapeutically effective amount of one or more H2 relaxin antagonist, wherein said antagonist has an amino acid modification in the B chain.

According to another aspect of the invention there is provided a method for the treatment of a tumor in a subject in need thereof by administering an effective amount of a H2 relaxin antagonist for a period of time sufficient to impair tumor growth and/or reduce the size of the tumor.

In aspects of the invention, the H2 relaxin antagonist inhibits binding of relaxin to the relaxin receptor.

According to another aspect of the invention is a composition for the treatment of tumors in a subject, said composition comprising a therapeutically effective amount of a H2 relaxin antagonist. In aspects, the H2 relaxin antagonist has one or more modifications in the receptor binding domain (RBD).

According to another aspect of the invention is a composition for the treatment of tumors in a subject, said composition comprising a therapeutically effective amount of a H2 relaxin antagonist having one or more modifications in the Arg-X-X-X-Arg-X-X-Ile motif of the receptor binding domain (RBD).

In aspects the modification is a substitution of amino acids at positions B13, B17 and/or B20 of the RBD. In further aspects, the modification is the substitution of a lysine residue at positions B13 and B17.

Compositions comprising a H2 relaxin antagonist useful in methods of the present invention can be formulated for administration in a variety of manners such as but not limited to infusion, injection, oral delivery and subcutaneously. In further aspects, intratumoral injections are employed.

According to still a further aspect of the invention is a method for making a H2 relaxin antagonist, the method comprising;

making one or more alterations to the receptor binding domain (RBD).

In aspects, the B13, B17 and/or B20 positions of the receptor binding domain are altered by the substitution of the amino acids located at one or more of these positions.

According to yet another aspect of the present invention is the use of a therapeutically effective amount of a H2 relaxin antagonist wherein said H2 relaxin antagonist has one or more modifications in the receptor binding domain (RBD) in the manufacture of a medicament for the treatment of cancer.

According to still a further aspect of the invention is a method for the treatment of prostate cancer in a subject, said method comprising administering a therapeutically effective amount of a relaxin antagonist selected from the group consisting of dH2, A1, A2, B1, B2, B3, C1, C2, D1, D2, D3, D4, D5, D6, D7, D8, D9 and combinations thereof; and optionally administering one or more other cancer therapies to said subject for a time sufficient to treat, reduce the cancer.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE INVENTION

Figure 1:
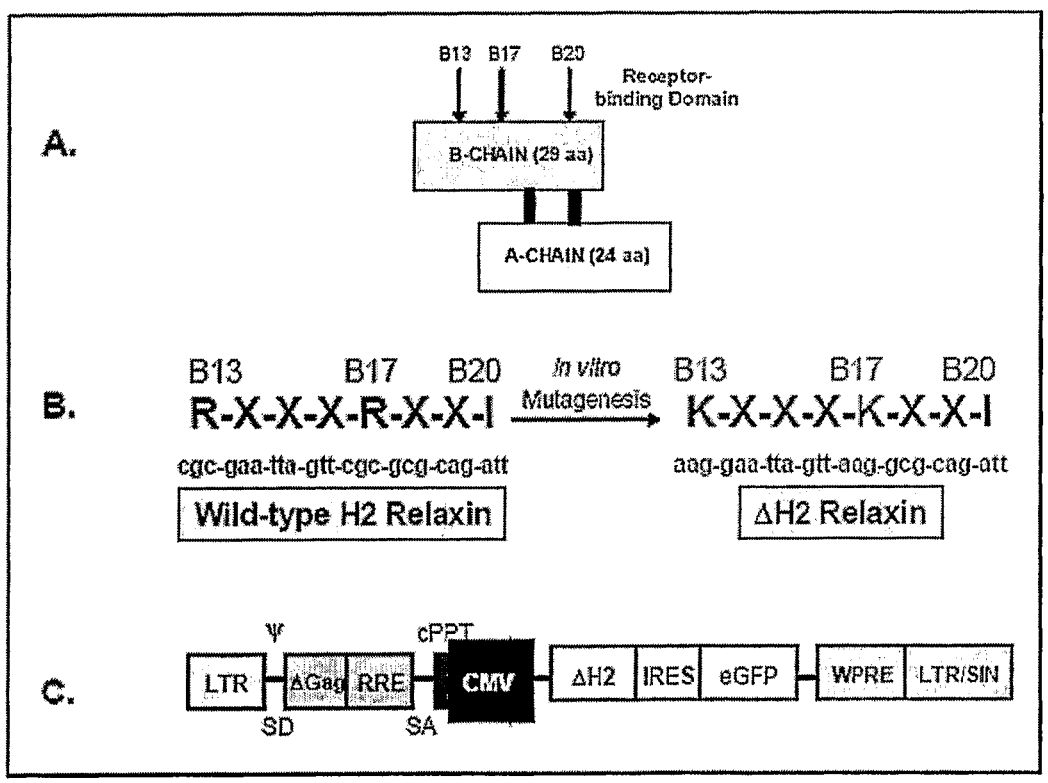
FIG. 1A is a schematic depicting the heterodimeric structure of H2 relaxin containing the A- and B-chains connected by two disulfide bridges and the RBD (consisting of amino acids B13, B17 and B20) present on the B-chain. 1B) Shows the amino acid and nucleotide sequences of the RBDs of wild-type H2 and ΔH2 relaxin after in vitro mutagenesis. 1C) shows a schematic of LV-cPPT-CMV-ΔH2-IRES-eGFP-WPRE (LV-ΔH2/eGFP) used in the present study. LTR: long-terminal repeat; SD: splice donor; RRE: rev response element; SA: splice acceptor; cPPT: central polypurine tract; CMV: cytomegalovirus promoter; WPRE: woodchuck hepatitis virus posttranscriptional regulatory element; IRES: encephalomyocarditis virus internal ribosomal entry site; eGFP: enhanced green fluorescent protein; SIN: self-inactivating LTR.

The present invention provides novel H2 relaxin antagonists. The H2 relaxin antagonists of the invention are demonstrated to reduce tumor size and as such can be used in a variety of compositions and methods to treat cancers by decreasing/suppressing/preventing tumor growth. The H2 relaxin antagonists of the invention bind to the relaxin receptor with high affinity and prevent the binding of relaxin. The relaxin antagonists of the invention effectively bind to the relaxin receptor without substantial receptor activation.

The relaxin H2 antagonists of the invention contain/comprise one or more modifications in the receptor binding domain located on the B-chain of H2 relaxin. In aspects the Arg-X-X-X-Arg-X-X-Ile motif is modified in a manner such that the modified relaxin retains the ability to bind to the relaxin receptor with high affinity without substantial activation of the receptor. In an aspect of the invention, the modifications may include but are not limited to: arginine mutants for B13 and B17 residues (using lysine/histidine); isoleucine mutants for B20 (using valine); and isoleucine/arginine mutants for B13, B17 and B20 residues (using combination of above). In a further non-limiting aspect of the invention, such a modification is a lysine substitution at positions B13 and/or B17 of the receptor binding domain. Such modification does not encompass in only certain embodiments of the invention substitution of the isoleucine residue at B20 with alanine. Further non-limiting embodiments of the relaxin H2 antagonists of the invention are shown in Tables A-D of the description. These antagonists are denoted as dH2, A1, A2, B1, B2, B3, C1, C2, D1, D2, D3, D4, D5, D6, D7, D8 and D9.

DEFINITIONS

The terms 'amino acid' or 'amino acid residue' as used herein, refer to L amino acids or to D amino acids as described herein. The commonly used one and three-letter abbreviations for amino acids are used herein (i.e. Alberts et al., Molecular Biology of the Cell, Garland Publishing Inc. New York, 3d. 1994). More specifically, the term "amino acid" refers to naturally occurring and synthetic amino acids, as well as amino acid analogues and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, and O-phosphoserine, phosphothreonine. "Amino acid analogues" refer to compounds that have the same basic chemical structure as a naturally occurring amino acid, i.e., a carbon that is bound to a hydrogen, a carboxyl group, an amino group, and an R group, for example, homoserine, norleucine, methionine sulfoxide, methionine methyl sulfonium. Such analogues have modified R groups (for example, norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid. Amino acids and analogues are well known in the art.

The term 'antagonist' in the context of a relaxin or relaxin receptor refers to an agent that binds to the relaxin receptor and reduces or inhibits the activity of the relaxin receptor.

The term 'modification' as used herein is synonymous with mutation, change, modification, switch, revision, permutation, alteration or derivative as is understood in the art. With respect to relaxin, a modified H2 relaxin is identified herein as ΔH2. Such ΔH2 may be provided by recombinant means, by chemical synthesis, as synthesized mimetics and as synthesized heterodimer peptides.

The term 'receptor binding domain' as used herein is located on the B-chain of relaxin and contains an Arg-X-X-X-Arg-X-X-Ile motif.

The term "cancer" in a mammal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

A "tumor," as used herein, refers to all neoplastic cell growth and proliferation, whether malignant or benign, and all precancerous and cancerous cells and tissues.

The term "effective amount" means a dosage sufficient to provide treatment for the disease state being treated. This will vary depending on the patient, the disease and the treatment being effected.

The term "relaxin" means human H2 relaxin, including full length relaxin (preprorelaxin) or a portion of the relaxin molecule (i.e. prorelaxin, mature relaxin, or short peptides of relaxin sequences) that retains biological activity and other active agents with relaxin-like activity, such as agents that competitively displace bound relaxin from a receptor. The cDNA and protein sequence of H2 relaxin is provided in Hudson, P. et al. Relaxin gene expression in human ovaries and the predicted structure of a human preprorelaxin by analysis of cDNA clones. *EMBO J.* 3: 2333-2339, 1984. Relaxin can be made by any method known to those skilled in the art as described in U.S. Pat. No. 4,835,251 and in U.S. Pat. No. 5,464,756 (PCT US90/02085) and PCT US94/06997 (the disclosures of which are incorporated herein by reference).

In one non-limiting embodiment of the present invention, mutation of the RBD by substitution of the B13 and B17 amino acid residues with lysine amino acid residues bestowed the peptide with the characteristics to retain affinity for the receptor while not inducing receptor-mediated intracellular signal transduction. Long-term LV-engineered expression of this H2 relaxin derivative (ΔH2) produces a molar excess of ΔH2 relaxin facilitating competition with endogenous relaxins for receptor binding and interfering with relaxin-induced signaling. To demonstrate ΔH2 relaxin as a therapeutic agent, PC-3 human prostate tumor xenografts were exposed long-term to ΔH2 relaxin as a clinical therapeutic agent to curb tumor growth. ΔH2 relaxin exhibited antagonistic properties in vitro and in vivo by blocking H2 relaxin-induced signaling and suppressing prostate xenograft tumor growth.

The substitution of the two conserved arginines present in the H2 relaxin RBD motif essentially impairs its biological function while retaining affinity for the receptor. As a result, ΔH2 relaxin exhibits antagonistic activity in vitro and in vivo and suppresses prostate tumor growth in a PC-3 tumor xenograft model.

Figure 2:
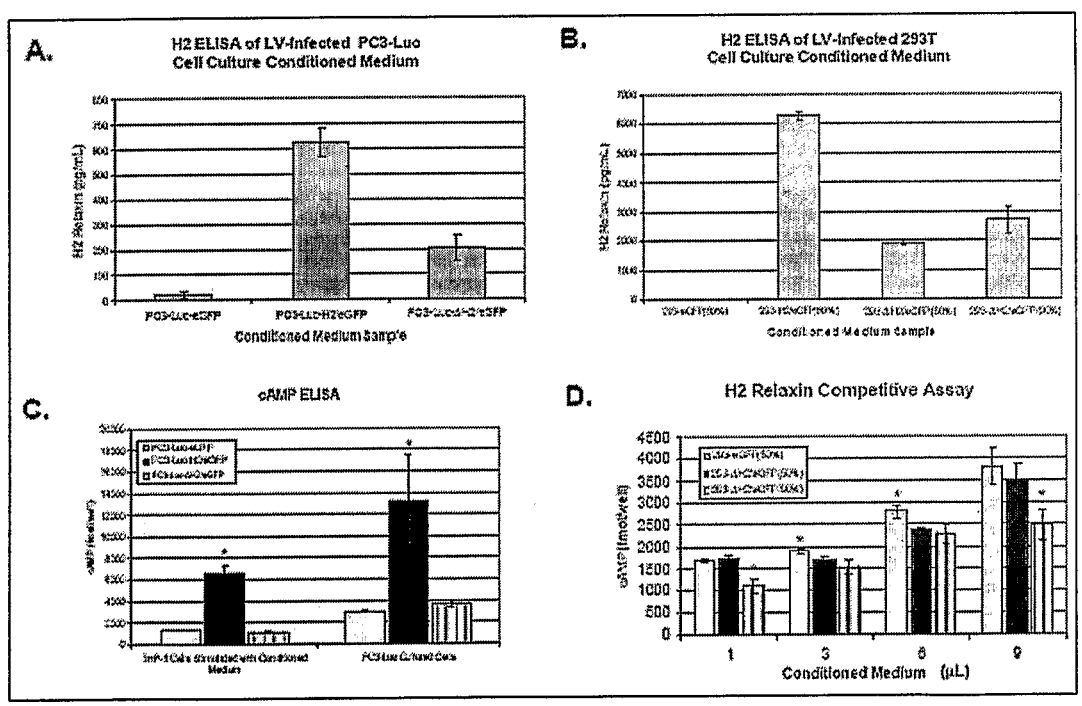
FIGS. 2A-D shows the expression and bioactivities of LV-engineered H2 and ΔH2 relaxins. H2 relaxin levels present in concentrated CM from LV-transduced 2A) PC3-Luc and 2B) 293T cell lines, as detected by an H2 relaxin ELISA. 2C) Bioactivity of ΔH2 is confirmed to be significantly impaired by cAMP assays in THP-1 and PC3-Luc cell cultures. PC3-Luc-H2/eGFP but not PC3-Luc-ΔH2/eGFP or PC3-Luc-eGFP cell cultures directly elicited significant expression of cAMP levels. Conditioned medium from PC3-Luc-H2/eGFP cell cultures but not from PC3-Luc cell cultures expressing ΔH2/eGFP or eGFP alone stimulates cAMP secretion from THP-1 cells. 2D) The THP-1 cAMP assay was adapted for a competitive assay to measure the antagonistic properties of ΔH2. THP-1 cells were co-incubated with 0.4 ng rH2 relaxin and varying volumes (1, 3, 6, 9 μL) of concentrated LV-infected 293T CM containing ΔH2 relaxin or control. Increasing amounts either 293T-ΔH2/eGFP (50%) or 293T-ΔH2/eGFP (90%) CM had a consistent and significant effect of reducing cAMP levels compared to 293T-eGFP (50%) control samples. Experiments were performed in triplicate and repeated three times.

The invention encompasses modification of residues within the vicinity of the amino acids reported to be essential for biological activity of H2 relaxin that may alter protein folding and final peptide conformation. While PC3-Luc (85% eGFP positive) and 293T (50% eGFP positive) cell culture samples had similar transduction rates for each LV (LV-H2/eGFP, LV-AH2/eGFP and LV-eGFP) as measured for eGFP by flow cytometry, data derived from H2 relaxin ELISAs show that Abs did not detect ΔH2 peptide as readily as wild-type H2 relaxin (FIGS. 2A and 2B). Antibody affinity to ΔH2 relaxin appears to be approximately 33% of the affinity that the ELISA Abs have for wild-type H2.

In a competition assay measuring H2 relaxin-induced cAMP release from THP-1 cells ΔH2 secreted from LV-infected 293T cell cultures competed with rH2 hormone for receptor binding (FIG. 2C). As the ratio of ΔH2:rH2 increased in each sample, greater suppression of secreted cAMP levels from THP-1 cells compared to eGFP controls was observed. While Abs employed in the H2 ELISA kit did not readily detect ΔH2 peptide from LV-infected PC3-Luc and 293T cvi culture CM, approximately 2 ng/mL of ΔH2 was detected. Significantly lower cAMP levels were consistently observed in THP-1 cultures incubated with CM from 293T-ΔH2 samples compared to the 293T-eGFP (50%) samples. This demonstrates that ΔH2 is impairing receptor signaling by competing with rH2 for relaxin receptor binding.

Figure 4:
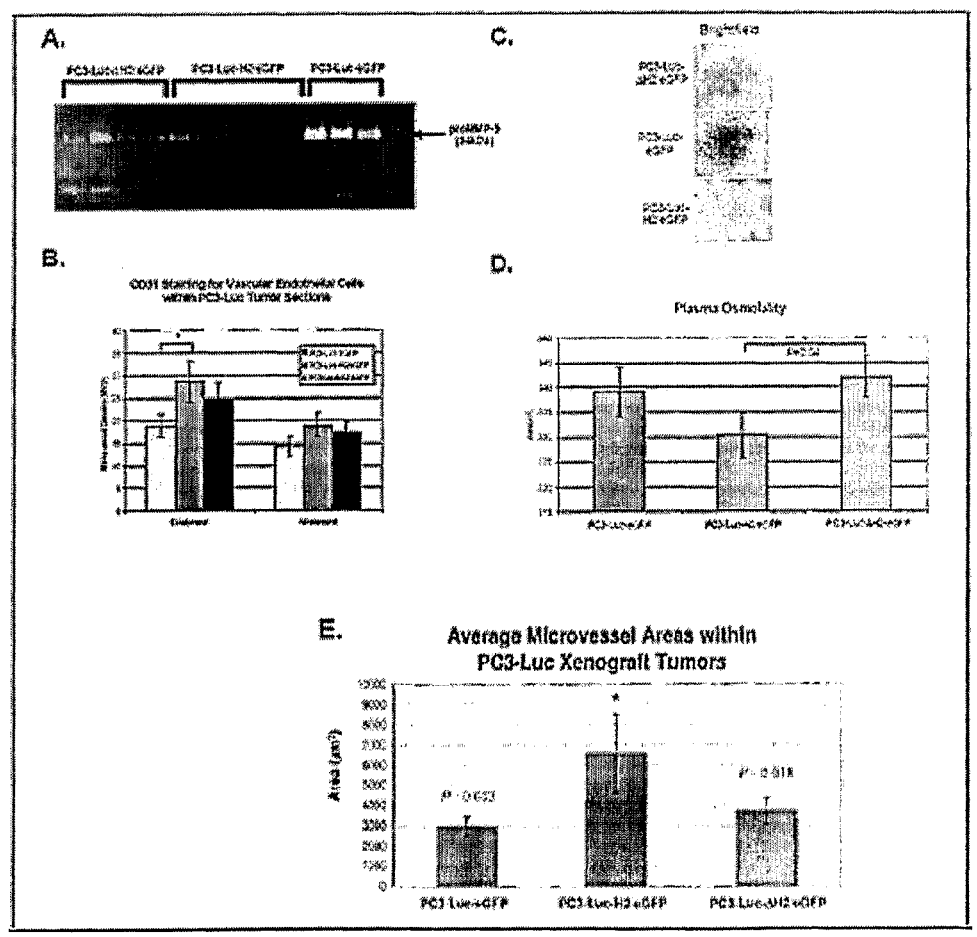
FIGS. 4A-E show that ΔH2 relaxin modulates physiological parameters in vivo. 4A) shows gelatin zymography employed to measure the effects of wild-type H2 and ΔH2 relaxins on PC3-Luc MMP-9 activity in vivo. A representative gelatin zymogram reveals the presence of gelatinase activity in tumor cell lysates (25 μg lane) from randomly selected PC3-Luc-ΔH2/eGFP, PC3-Luc-H2/eGFP and PC3-Luc-eGFP tumor samples. Gelatin zymographies were repeated 4 times. 4B) shows microvessel density (MVD) of vascular endothelial cells (ECs) present in intra-tumoral and extra-tumoral 'hot spots' within tumor sections identified using mouse anti-CD31 antibodies. Leveled sections were obtained from four distinctly different regions of each tumor. Within each section, regions of increased density of vascular ECs termed 'hot spots' were identified under low magnification at 100×. To determine MVD, vascular ECs present in four of the densest intra-tumoral 'hot spots' within each section were counted at 200× magnification and averaged. 4C) shows images of PC3-Luc colony spheres at week 5 grown in a soft agarose colony assay. 4D) shows plasma osmolality readings from blood collected from animals at week 11; PC3-Luc-ΔH2/eGFP (n=6), PC3-Luc-H2/eGFP (n=4), and PC3-Luc-eGFP (n=6). 4E) shows average microvessel areas (MVA) present within PC3-Luc tumors. Under ×400 magnification, areas were calculated from 9-12 of the largest microvessels within each section (n=2-4) of each tumor. Total MVAs for each treatment group were calculated y averaging the MVAs from several sections of each tumor within the group.

In three distinct animal models, LV-engineered overexpression of ΔH2/eGFP results in suppressed prostate tumor xenograft growth compared to tumors overexpressing wild-type H2/eGFP or control tumors overexpressing eGFP. Without being bound to any theory, tumor-expressed ΔH2 relaxin may be neutralizing available receptors in an autocrine fashion, thereby blocking endogenous H2 signaling. The precise pathways that LGR7 and LGR8 may regulate to facilitate tumor growth are not known, but an antagonist may abrogate endogenous H2-mediated pathways altering cellular proliferation, gene expression, and neoangiogenesis (Bathgate, R. A., Ivell, R., Sanborn, B. M., Sherwood, O. D., Summers, R. J. 2005. Receptarc for relaxin family peptides. Ann NY Acad Sci. 1041:61-76). For example, the putative antagonistic activity demonstrated by ΔH2 relaxin was evidenced by intermediate levels of MMP-9 activity (an established downstream effector in H2 relaxin signaling) in ΔH2 relaxin-expressing tumors compared to lower and higher levels in H2/eGFP and eGFP-expressing tumors, respectively (FIG. 4A). Moreover, effects of ΔH2 relaxin were also observed in tumoral MVD, a measure of the indirect influence H2 relaxin may have on promoting angiogenesis. Sections from ΔH2 relaxin-expressing tumors exhibited intermediate values of CD31-positive staining for vascular ECs. Taken together, the ΔH2 hormone analogue antagonist appears to be partially interfering with the endogenous functions of H2 relaxin in PC3-Luc tumors by acting on relaxin receptors to alter cellular signaling pathways.

Circulating H2 relaxin in the rodent (most notably during pregnancy) results in cardiovascular changes leading to osmoregulatory imbalances (i.e. changes in plasma osmolality) (Sunn, N., Egli, M., Burazin, T. C., Burns, P., Colvill, L., Davern, P., Denton, D A., Oldfield, B. J., Weisinger, R. S., Rauch, M., Schmid, H. A., McKinley, M. J. 2002. Circulating relaxir acts on subformical organ neurons to stimulate water drinking in the rat. Proc Nail Ac2Yi Sci USA. 99:1701-1706). Relaxin KO mice exhibit a phenotype with an increased plasma osmolality of 10 mosmol/kg water compared to wild-type mice (Zhao, L., Roche, P. J., Gunnersen, J. M., Hammond, V. E., Tregear, G. W., Wintour, E M., Beck, F. 1999. Mice without a functional relaxin gene are unable to deliver milk to their pups. *Endocrinology.* 140:445-453). Moreover, delivery of human H2 relaxin i.v or cv in the rat causes reductions in plasma osmolality (Weisinger, R. S., Burns, P., Eddie, L. W., Wintour, E. M. 1993. Relaxin alters the plasma osmolality-arginine vasopressin relationship in the rat. *J Endocrinol.* 137:505-510; Silvertown, J. D., Fraser, R., Poterski, R. S., Geddes, B., Summerlee, A. J. 2005. Central effects of long-term relaxin expression in the rat. *Ann NY Acad Sd.* 1041:216-22). In the present invention, changes in plasma osmolality were investigated as an approach to measure the paracrine influence of tumor secreted ΔH2 relaxin. Plasma osmolality readings were approximately 12 mmol/L higher (P=0.04) in ΔH2-expressing tumors compared to wild-type H2-expressing tumors demonstrating that ΔH2 may be blocking endogenous ligand binding to relaxin receptors in the pituitary gland or other regions in the mouse and affecting osmoregulation.

Relaxin Antagonists

The present invention broadly provides novel H2 relaxin antagonists where such antagonists comprise one or more alterations of the B chain that retains binding of the peptide to its receptor, however, does not substantially activate the receptor once bound thereto. In one embodiment the Arg-X-X-X-Arg-X-X-Ile motif of the B chain is modified in a manner such that the modified relaxin retains the ability to bind to the relaxin receptor with high affinity without substantial activation of the receptor. In an aspect of the invention, the modifications may include but are not limited to: arginine mutants for B13 and B17 residues (using lysine/histidine); isoleucine mutants for B20 (using valine); and isoleucine/arginine mutants for B13, B17 and B20 residues (using combination of above).

Again, the feature of the invention is an alteration of the B-chain of H2 relaxin that leads to receptor binding of the modified protein without substantial activation of the receptor. Receptor binding and activation can be measured as readily understood by one of skill in the art as taught herein in the example 1 discussing in vitro cAMP bioassays.

The following tables represent non-limiting examples of suitable amino acid substitutions at positions B13, B17 and B20 of the B chain relaxin binding domain that are within the scope of the present invention.

TABLE A

| | Valine Mutants | | |
|---|---|---|---|
| | B13 | B17 | B20 |
| WT | Arg | Arg | Ile |
| D2 | Arg | Arg | Val |

TABLE A-continued

Valine Mutants

|     | B13 | B17 | B20 |
| --- | --- | --- | --- |
| D3  | Lys | Arg | Val |
| D4  | Arg | Lys | Val |
| D5  | Lys | Lys | Val |
| D6  | His | Arg | Val |
| D7  | Arg | His | Val |
| D8  | His | His | Val |
| D9  | His | Lys | Val |
| D10 | Lys | Lys | Val |

TABLE B

Lysine Mutants

|     | B13 | B17 | B20 |
| --- | --- | --- | --- |
| WT  | Arg | Arg | Ile |
| dH2 | Lys | Lys | Ile |
| A1  | Lys | Arg | Ile |
| A2  | Arg | Lys | Ile |

TABLE C

Histidine Mutants

|     | B13 | B17 | B20 |
| --- | --- | --- | --- |
| WT  | Arg | Arg | Ile |
| B1  | His | His | Ile |
| B2  | His | Arg | Ile |
| B3  | Arg | His | Ile |

TABLE D

Lysine/Histidine Mutants

|     | B13 | B17 | B20 |
| --- | --- | --- | --- |
| WT  | Arg | Arg | Ile |
| C1  | His | Lys | Ile |
| C2  | Lys | Lys | Ile |

In non-limiting aspects of the invention, the H2 relaxin receptor antagonists of the present invention include but are not limited to those identified in the above tables as: dH2, A1, A2, B1, B2, B3, C1, C2, D1, D2, D3, D3, D4, D5, D6, D7, D8 and D9. The amino acid alterations are shown in the tables. It is understood by one of skill in the art that the invention encompasses any altered RBD relaxin peptide and in aspects those described herein. The invention also encompasses the use of such relaxin antagonists in a variety of compositions and methods to treat cancer where one or more such antagonists are selected from dH2, A1, A2, B1, B2, B3, C1, C2, D1, D2, D3, D3, D4, D5, D6, D7, D8 and D9. Any combination of these can be used, for a non-limiting example the dH2 (double lysine mutant) can be used alone for treatment or in combination with one or more of the other noted relaxin antagonists and so on. In further aspects of the invention the relaxin antagonists A2, B1, B2, B3, C1, C2, D3, D4 and D7 are used.

Again included within the scope of the term "H2 relaxin receptor antagonist" are ΔH2 proteins (polypeptides) comprising insertions, substitutions, or deletions of one or more amino acid residues of the RBD sequence at any position from B13 to B20. Furthermore, the ΔH2 polypeptides of the invention may further be altered with glycosylation, unglycosylation, organic and inorganic salts and covalently modified. Also encompassed are ΔH2 polypeptides modified to increase in vivo half life, e.g., PEGylated (i.e., ΔH2 polypeptides conjugated to a polyethylene glycol), and the like.

As shown in the tables A-D above, possible but non limiting modifications to the relaxin RBD polypeptide include replacement of one or more of the natural amino-acids in the B chain with a different amino acid (including the D-form of a natural amino-acid). Other possible non-limiting modifications include the deletion of a natural amino acid from the chain or the addition of one or more extra amino acids to the chain. Of course, modifications may also comprise combinations of amino acid substitutions together with a deletion of one or more amino acids or the addition of one or more amino acids.

Also encompassed within the scope of the invention are fusion ΔH2 polypeptides comprising a ΔH2 polypeptide and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors. Fusion proteins and methods of making are disclosed for example in U.S. Pat. Nos. 5,326,694, 5,320,953, 5,179,195 and 5,053,488 (the disclosures of which are incorporated herein by reference.

All such variations or alterations in the structure of H2 relaxin resulting in variants are included within the scope of this invention so long as the functional (biological) activity of the H2 relaxin is maintained, i.e. binding to its receptor. In general, any modification of relaxin amino acid sequence or structure is one that does not increase its immunogenicity in the individual being treated with the relaxin variant. Those variants of relaxin having the described functional activity can be readily identified using the methods discussed herein.

Antagonist Therapy

In one embodiment, the invention involves the use of the novel H2 relaxin antagonists in compositions and methods to treat cancer. It is understood to those of skill in the art that any H2 relaxin antagonist that binds to the relaxin receptor such that wild type relaxin binding is prevented/decreased and also does not essentially cause relaxin receptor activation leading to intracellular signaling is encompassed in the invention.

An embodiment of the present invention further encompasses pharmaceutical compositions comprising one or more H2 relaxin receptor antagonists as described herein for administration to subjects in a biologically compatible form suitable for administration in vivo. By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of preventing or minimizing the receptor activation response leading to decrease of tumor size or prevention/minimizing of tumor growth. In aspects this is a reduction or prevention of cancerous cell growth in any tissues and organs where the cells express relaxin receptors.

A therapeutically effective amount of a substance may vary according to factors such as the disease state/health, age, sex, and weight of the recipient, and the inherent ability of the particular antagonist to elicit a desired response. Dosage regima may be adjusted to provide the optimum therapeutic response and may be at the discretion of the attending physician or veterinarian. For example, several divided doses may be administered daily or on at periodic intervals, and/or the dose may be proportionally reduced as indicated by the exigencies of the therapeutic situation. The amount of relaxin antagonist for administration will depend on the route of administration, time of administration and varied in accordance with individual subject responses. Suitable administration routes are intramuscular injections, subcutaneous injections, intravenous injections or intraperitoneal injections, oral and intranasal administration. In particular embodiments of the invention, the desired administration is intratumorally. In other embodiments oral administration may be in conjunction with trypsin/protease inhibitors. Compositions comprising the relaxin antagonists of the invention may comprise about 0.1% to about 90% by weight of the active and any range there-in-between.

In one aspect of the invention, the ΔH2 antagonists of the invention are provided to those in need of treatment thereof by intravenous administration, for example, by injection of a unit dose. The term "unit dose" when used in reference to a pharmaceutical composition of the present invention refers to physically discrete units suitable as unitary dosage for humans, each unit containing a predetermined quantity of active material calculated to produce the desired therapeutic effect in association with the required diluent; i.e., liquid used to dilute a concentrated or pure substance (either liquid or solid), making that substance the correct (diluted) concentration for use. For injectable administration, the composition is in sterile solution or suspension or may be emulsified in pharmaceutically- and physiologically-acceptable aqueous or oleaginous vehicles, which may contain preservatives, stabilizers, and material for rendering the solution or suspension isotonic with body fluids (i.e., blood) of the recipient. Excipients suitable for use are water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as routes of administration, used are determined on an individual basis, and correspond to the amounts used in similar types of applications or indications known to those of skill in the art.

For oral administration it is desirable to provide the ΔH2 antagonists of the invention with protease inhibitors (i.e. trypsin inhibitors, pepstatin A, leupeptin, etc) known to minimize/prevent the degradation of the ΔH2 peptide in the gut as is understood by those of skill in the art.

The ΔH2 antagonist may be administered over a period of hours, days, weeks, or months, depending on several factors, including the severity of the disease being treated, whether a recurrence of the disease is considered likely, etc. The administration may be constant, e.g., constant infusion over a period of hours, days, weeks, months, etc. Alternatively, the administration may be intermittent, e.g., relaxin may be administered once a day over a period of days, once an hour over a period of hours, or any other such schedule as deemed suitable.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

It is also understood by those of skill in the art that cell lines as disclosed herein may be used in various methods to screen a variety of relaxin antagonists for their ability to inhibit the binding of relaxin to its receptor or inhibit downstream receptor intracellular signaling. For example, screening may be done for the ability of the relaxin antagonist to interfere with the downstream intracellular signaling system activated with the binding of relaxin to the relaxin receptor. Such identified relaxin antagonists having modifications made therein may also be used therapeutically as described herein.

The present invention provides systemic delivery of recombinant ΔH2 relaxin to treat cancers in mammals where the relaxin receptor is expressed. Thus the present invention encompasses treatment of any cancer where the relaxin receptor is expressed with the modified relaxin antagonists of the invention. In particular, the relaxin receptor is expressed in reproductive tissues in males and females and therefore the invention has particular utility in the treatment of any reproductive cancer in both men and women. As such, the modified relaxin antagonist of the invention may be used to treat prostate tumors. In addition, because relaxin has been implicated in several other types of neoplasias, including those originating in the thyroid (Hombach-Klonisch, S., Hoang-Vu, C., Kehlen, A., Hinze, P., Holzhausen, H. J., Weber, E. Fischer, B., Dralle, H., Klonisch, T. 2003. INSL-3 is expressed in human hyperplastic and neoplastic thyrocytes. *Int J Oncol.* 22:993-1001) and breast (Tashima, L. S., Mazoujian, G., Bryant-Greenwood, G D. 1994 Human relaxins in normal, benign and neoplastic breast tissue. *J Mol. Endocrinol.* 12:351-64) further modifications of the RBD within H2 relaxin and other relaxin-like peptides may also offer therapeutic intervention strategies for a variety of cancers such as but not limited to prostate, breast, thyroid, colorectal, endometrial, ovarian, leukemia, lymphoma, testicular, glioma and astrocytoma. As the relaxin receptor is expressed in reproductive tissues/organs the antagonists of the invention have utility in the treatment of any cancers relating to the reproductive tissues/organs in males and females.

It is understood by those of skill in the art that the modified H2 relaxin antagonist of the invention may be used to treat mammals in general including humans and a variety of animals. Thus the invention has wide potential use for both humans and in the veterinary field.

It is further understood by those of skill in the art that the compositions herein described may be used in conjunction with other therapeutic agents and other therapeutic treatments including those currently known for the treatment of a wide variety of cancers such as chemotherapy. The most common routes of administration for chemotherapy are oral, intravenous, and intramuscular. More recently, other methods have been used to increase the local concentration of chemotherapeutic agents at a tumor site. For example, chemotherapy may be administered by arterial perfusion, be administered directly into a specific cavity (intracavitary), the abdomen (intraperitoneal), the lung (intrapleural), or the central nervous system (intrathecal), or may be applied directly to the skin (topical). If desired, the relaxin antagonists of the invention may be administered by the same route as the chemotherapeutic agent, even if they are not administered simultaneously. The modified relaxin antagonist peptides of the invention may be administered individually, or in combination with other antagonists or inhibitors. The relaxin antagonists of the invention may also be administered in various combinations thereof, that is, one or more of the relaxin antagonists described herein may be used in a single composition or in an alternating treatment manner.

The disclosed modified relaxin antagonist peptides can be used in combination with other cancer therapies, e.g., surgery, radiation, biological response modification, immunotherapy, anti-hormone therapy, anti-androgen therapy and/or chemotherapy. In aspects of the invention for prostate cancers, non-limiting examples of chemotherapeutic agents include docetaxel, paclitaxel, estramustine, etoposide, vinblastine, mitoxantrone, and paclitaxel. Anti-androgen drugs such as Zoladex, Casodex, Plenaxis, Eligard, Lupron, etc., are also useful for treatment of prostate cancer in conjunction with the present invention. For breast cancers, non-limiting examples of chemotherapeutic and biological agents include cyclophosphamide, methotrexate, 5-fluorouracil, doxorubicin, tamoxifen, paclitaxel, docetaxel, navelbine, capecitabine, mitomycin C, Interferons, interleukin-2, lymphocyte-activated killer cells, tumor necrosis factors, and monoclonal antibodies (e.g., mAb to HER-2/neu receptor (trastuzumab) Herceptin™).

The ΔH2 of the invention can also be administered to an individual in the form of a polynucleotide comprising a nucleotide sequence which encodes ΔH2. The ΔH2 can be administered to an individual in the form of a polynucleotide comprising a nucleotide sequence which encodes ΔH2. Such ΔH2 encoding nucleotide sequences can be readily determined, any of which can be used in the methods described herein. The ΔH2 antagonist polynucleotides and polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly, Cancer Gene Therapy (1994) 1:51-64; Kimura (1994) Human Gene Therapy 5:845-852; Connelly (1995) Human Gene Therapy 1:185-193; and Kaplitt (1994) Nature Genetics 6:148-153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 415 731; WO 90/07936; WO 94/03622; WO 93/25698; WO 93/25234; U.S. Pat. No. 5,219,740; WO 93/11230; WO 93/10218; Vile and Hart (1993) Cancer Res. 53:3860-3864; Vile and Hart (1993) Cancer Res. 53:962-967; Ram et al. (1993) Cancer Res. 53:83-88; Takamiya et al. (1992) J. Neurosci. Res. 33:493-503; Baba et al. (1993) J. Neurosurg. 79:729-735; U.S. Pat. No. 4,777,127; and EP 345,242. A subgroup of retroviruses, a lentivirus, may be employed as vectors (lentivectors) for expression of modified H2 relaxin (Science 272, 263-267 (1996). Lentivectors are used for efficient delivery of expression constructs in mammalian systems, Such vectors are commercially available as described herein and also as described in U.S. Pat. No. 6,498,033, U.S. Pat. No. 6,521,427 and U.S. Pat. No. 6,531,123. Lentiviral vectors were used in the present invention to overexpress the ΔH2 protein.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

Gene delivery vehicles of the present invention can also employ parvovirus such as adeno-associated virus (AAV) vectors. Representative examples include the AAV vectors disclosed by Srivastava in WO 93/09239, Samulski et al. (1989) J. Vir. 63:3822-3828; Mendelson et al. (1988) Virol. 166:154-165; and Flotte et al. (1993) Proc. Natl. Acad. Sci. USA 90:10613-10617. Also are adenoviral vectors, e.g., those described by Berkner, Biotechniques (1988) 6:616-627; Rosenfeld et al. (1991) Science 252:431-434; WO 93/19191; Kolls et al. (1994) Proc. Natl. Acad. Sci. USA 91:215-219; Kass-Eisler et al. (1993) Proc. Natl. Acad. Sci. USA 90:11498-11502; WO 94/12649, WO 93/03769; WO 93/19191; WO 94/28938; WO 95/11984 and WO 95/00655.

Other gene delivery vehicles and methods may be employed, including polycationic condensed DNA linked or unlinked to killed adenovirus alone, for example Curiel (1992) Hum. Gene Ther. 3:147-154; ligand linked DNA, for example see Wu (1989) J. Biol. Chem. 264:16985-16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) Mol. Cell. Biol. 14:2411-2418, and in Woffendin (1994) Proc. Natl. Acad. Sci. 91:1581-1585.

The recombinant constructs of the present invention for expressing ΔH2 may include a selectable marker for propagation and screening of the construct. Selectable markers include, but are not limited to, genes that confer antibiotic resistance, (e.g., resistance to kanamycin or hygromycin. Screenable markers include, but are not be limited to, reporter genes encoding β-glucuronidase (Jefferson, 1987, Plant Mol. Biol. Rep. 5:387 405), luciferase (Ow et al., 1986, Science 234:856 9), fluorescent proteins (such as GFP as described in Kain et al., 1995, Biotech. 19:650 5; blue GFP as described by Heim and Tsien, 1996, Curr. Biol. 6:178 82; or yellow and red GFP as described by Matz et al., 1999, Nature Biotechnol. 17:969 73).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Further non-viral delivery suitable for use includes mechanical delivery systems such as the approach described in Woffendin et al. (1994) Proc. Natl. Acad. Sci. USA 91:11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033. The H2 relaxin polynucleotides and polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly, Cancer Gene Therapy (1994) 1:51-64; Kimura (1994) Human Gene Therapy 5:845-852; Connelly (1995) Human Gene Therapy 1:185-193; and Kaplitt (1994) Nature Genetics 6:148-153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

Antagonist Synthesis

The H2 relaxin antagonist of the invention (ΔH2), for either systemic or local administration, may be synthesized either by standard techniques of recombinant polypeptide production (see, e.g., Ausubel et al., Current Protocols in Molecular Biology, John Wiley & Sons, New York, 1997; Sambrook et al., Molecular Cloning, A Laboratory Manual, 2nd ed., Cold Spring Harbor Press, Cold Spring Harbor, N.Y., 1989) or by peptide synthesis (e.g., by the methods described in Solid Phase Peptide Synthesis, 2nd ed., 1984 The Pierce Chemical Co., Rockford, Ill.). In one aspect of the invention, site-directed mutagenesis was employed to provide alterations in the RBD. H2 Relaxin gene and polypeptide sequences are provided, e.g., in Hudson et al., Nature 301:628-631, 1983; Hudson et al., EMBO J. 3:2333-2339, 1984; and Gunnersen et al., J. Mol. Endocrinol. 15: 153-166, 1995. The ΔH2 may be demonstrated to be functional, e.g., in the bioassays of Fei et al. (Biochem. Biophys. Res. Comm. 170:214-222, 1990), Kramer et al. (In Vitro Cell. Dell. Biol. 26:647-656, 1990), and Parsell et al (7), and in the mouse pubic symphysis assay (Bullesbach and Schwabe, Biochemistry 25:5998-6004, 1986) are also useful in the invention. Methods and assays for making the ΔH2 relaxin of the invention are described herein in the example section.

The present invention also contemplates non-peptide analogues of the ΔH2 peptides of the invention, e.g. peptide mimetics that provide a stabilized structure or lessened biodegradation. Such peptide mimetics are designed based on the structure and function of the ΔH2 peptides and thus retain the ability of being to the relaxin receptor without substantial activation thereof. Thus they also function as antagonists of the relaxin receptor. Peptide mimetic analogues can be prepared based on any desired ΔH2 peptide. Preferably, the non-peptide moieties permit the peptide to retain its natural conformation, or stabilize a preferred, e.g. bioactive confirmation. Such peptides can be tested in molecular or cell-based binding assays to assess the effect of the substitution(s) on conformation and/or activity as described herein. The preparation of non-peptide mimetic analogues from the peptides of the invention can be done, for example, as taught in Nachman et al., *Regul. Pept.* 57: 359-370 (1995).

The present invention also encompasses nucleic acid molecules comprising a nucleotide sequence which encodes one or more selected ΔH2 peptides encompassed herein having a sequence where one or more amino acids are altered at positions B13, B14, B15, B16, B17, B18, B19 and/or B20 of the B chain as well as variants thereof.

Also encompassed by the present invention are nucleic acid sequences which are complementary as well as anti-complementary to a sequence encoding and equivalent sequence variants thereof. One skilled in the art would readily be able to determine such complementary or anti-complementary nucleic acid sequences. Also as part of the invention are nucleic acid sequences which hybridize to one of the aforementioned nucleic acid molecules under stringent conditions. “Stringent conditions” as used herein refers to parameters with which the art is familiar and such parameters are discussed, for example, in the latest editions of Molecular Cloning: A Laboratory Manual, J. Sambrook, et al., eds., Cold Spring Harbor Laboratory Press, Cold Spring Harbor, N.Y., or Current Protocols in Molecular Biology, F. M. Ausubel, et al., eds., John Wiley & Sons Inc., New York. One skilled in the art would be able to identify homologues of nucleic acids encoding the ΔH2 antagonists of the invention. Cells and libraries are screened for expression of such molecules which then are routinely isolated, followed by isolation of the pertinent nucleic acid molecule and sequencing.

It is noted that the nucleic acid molecules described herein may also encompass degenerate nucleic acids. Due to degeneracy in the genetic code, variations in the DNA sequence will result in translation of identical peptides. It is thus understood that numerous choices of nucleotides may be made that will lead to a sequence capable of directing production of the peptides or functional analogues thereof of the present invention. As a result, degenerative nucleotide substitutions are included in the scope of the invention.

As would be understood by one of skill in the art, nucleic acid molecules of the present invention may encompass single and double stranded forms, plasmid(s), viral nucleic acid(s), plasmid(s) bacterial DNA, naked/free DNA and RNA. A viral nucleic acid comprising a nucleic acid sequence encoding for at least one peptide of the invention may be referred to as a viral vector.

The invention also encompasses expression vectors for synthesizing of the protein comprising the nucleic acid sequences of the invention encoding one or more of the ΔH2 antagonists having a sequence disclosed herein where one or more amino acids are altered at positions B13, B14, B15, B16, B17, B18, B19 and/or B20 of the B chain and functional analogues thereof within expression vectors. Any expression vector that is capable of carrying and expressing the nucleic acid sequences encoding for the peptides of the invention and functional analogues thereof in prokaryotic or eukaryotic host cells may be used, including recombinant viruses such as poxvirus, adenovirus, alphavirus and lentivirus.

The invention also encompasses host cells transformed, transfected or infected with such vectors to express the peptides or functional analogues of the invention. As such, host cells encompass any potential cell into which a nucleic acid of the present invention may be introduced and/or transfected.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Characterization of Mutated H2 Relaxin (ΔH2)

Figure 3:
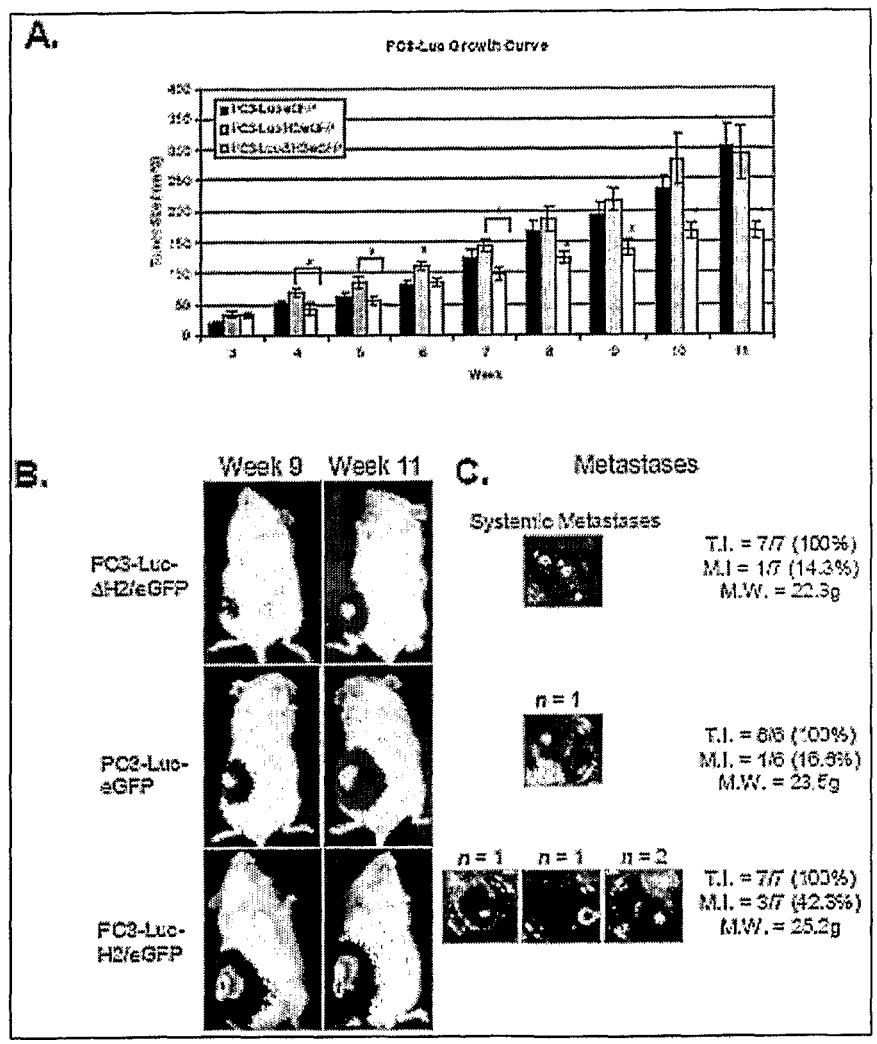
FIGS. 3A-C show that PC3-Luc prostate xenograft tumors overexpressing ΔH2 relaxin exhibit reduced growth. LV-infected PC3-Luc cells ($2\times10^6$) were implanted s.c in the dorsal right flank of NOD/SCID mice (n=6 or 7 per group). 3A) shows weekly tumor measurements by calipers up to 11 weeks after implantation. 3B) shows representative BLI images of the same PC3-Luc-ΔH2/eGFP, PC3-Luc-eGFP, and PC3-Luc-H2/eGFP xenograft tumor-bearing mice at weeks 9 and 11. 3C) shows metastatic tissues identified in animals excised and imaged for luciferase expression to confirm origin from PC3-Luc prostate xenograft tumors. (Note: a representative metastatic tumor image from the PC3-Luc-H2/eGFP samples was used to illustrate the metastatic tumor found in a single mouse from the PC3-Luc-eGFP tumor-bearing mice.) T.I: tumor incidence; MI: metastasis incidence; M.W: average mouse weight; n=number of metastatic tumors found in respective animal. Asterisk (*) indicates $P<0.05$.

The H2 relaxin cDNA was subjected to in vitro site-directed mutagenesis to alter two of the three residues determined critical for relaxin receptor binding (FIGS. 1A and 1B). The two arginines at B13 and B17 were replaced with nucleotides encoding lysine residues (Bullesbach, E. E., Yang, S., Schwabe, C. 1992. The receptor-binding site of human relaxin H. A dual prong-binding mechanism. *J Bio Chem.* 267:22957 60); the other amino acid critical for binding (isoleucine at B20) was left intact (FIG. 1 B).

To produce ΔH2 relaxin, a novel recombinant LV engineering the expression of ΔH2 relaxin was constructed (FIG. 1C) as described previously (Silvertown, J. D., Ng, J., Sato, T., Summerlee, A. J., Medin, J. A. 2006. H2 relaxl; overexpression increases in vivo prostate xenograft tumor growth and angiogenesis. *Iift J Cancer.* 118:62-73). PC3-Luc cells, a PC-3 clonally-derived human prostate cancer cell line expressing luciferase (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73), transduced with LV-ΔH2/eGFP, LVH2/eGFP or LV-eGFP were sorted by flow cytometry to isolate eGFP-positive cells. Populations of PC3-Luc cells expressing either eGFP alone, or in a bicistronic format with either H2 or ΔH2 relaxin, were characterized to be ~85% positive for fluorescent protein expression. These cell populations were termed PC3-Luc-eGFP, PC3-Luc-H2/eGFP and PC3-Luc-ΔH2/eGFP, respectively (data not shown). 293T cells were also transduced with an appropriate volume of each LV stock to generate three cell lines that were ~50% positive for eGFP [293T-H2/eGFP (50%), 293T ΔH2/eGFP (50%), and 293T-eGFP (50%)] and one cell line that was ~90% positive for eGFP [293T-ΔH2/eGFP (90%)], as determined by flow cytometry analysis (data not shown). In FIGS. 2A and 2B, concentrated conditioned medium (CM) from PC3 Luc-H2/eCV- and 293T-H2/eGFP (50%) samples contained significant levels of H2 relaxin compared to basal or undetectable levels in the PC3-eGFP and 293T eGFP (50%) samples, respectively. Unexpectedly, ΔH2 was detected at lower concentrations in these cell culture samples compared to H2-expressing cells but higher than eGFP-expressing controls. Since transduced cells had similar expression levels of the downstream eGFP marker, lower levels of AH2 suggest a potential reduction of Ab affinity in the ELISA possibly due to changes in structural conformation. As expected, 293T-ΔH2/eGFP (90%) samples had proportionately greater ΔH2 relaxin levels compared to 293T-ΔH2eGFP (50%) samples.

Mutation of the relaxin RBD (R-X-X-X-R-X-X-I to K-X-X-X-K-X-X-I) rendered the molecule non-stimulatory (FIG. 2C), as confirmed by an in vitro THP-1 cAMP bioassay (Parse D. A., Mak, J. Y., Amento, E P., Unemori, E. N. 1996. Relaxin binds to and elicits a response from cells of the human monocytic cell line, THP-1. *J Biol. Chem.* 271: 27936-41). THP-1 cells incubated with CM from PC3-Luc-H2/eGFP cultures elicited a substantial increase in total cAMP from cultures (6599±674 fmol/well) compared to basal levels present in both PC3-Luc-ΔH2/eGFP (1018±45 fmol/well) and PC3-Luc-eGFP (1218±25 fmol/well) samples. PC3-Luc-H2/eGFP cells were found to contain 13,221±41.85 fmol/well total cAMP compared with PC3-Luc ΔH2/eGFP and PC3-Luc-eGFP cell cultures which contained equally lower levels of cAMP.

Since ΔH2 relaxin was observed to be nonfunctional while retaining some affinity for receptor binding (Bullesbach, E. E., Yang, S., Schwabe, C. 1992. The receptor-binding site of human relaxin H. A dual prong-binding mechanism. *J Biol. Chem.* 267:22957-60), it was hypothesized that ΔH2 (at high levels) may act as an antagonist and competitively inhibit H2 relaxin binding. Therefore, in another set of experiments, the THP-1 cAMP assay was adapted as a competitive assay to measure the antagonistic properties of Alt relaxin (FIG. 2D). Concentrated CM from LV transduced 293T cells was used because 293T cells secrete relatively high levels of recombinant H2 relaxin (as above). THP-1 cells were uniformly co-incubated in 96 well plates with 0.4 ng recombinant H2 relaxin (rH2) and increasing CM volumes from either 293T-ΔH2/eGFP (50%) or 293T-ΔH2/eGFP (90%) cell cultures. 293 ΔH2/eGFP CM samples had a consistent effect of reducing cAMP levels compared to control 293T-eGFP (50%) CM samples (FIG. 2D). Addition of increasing sample volumes (1, 3, 6, or 9 μL) of 293T-ΔH2/eGFP (90%) CM samples, that contained nearly 2-fold more ΔH2 hormone than 293T-ΔH2/eGFP (50%) samples (FIG. 2B), resulted in greater suppression of total cAMP release from THP-1 cells. Taken together, these results suggest that the ΔH2 hormone is competing rH2 for relaxin receptor binding on THP-1 cells.

Example 2

Effect of Overexpression of ΔH2 Relaxin in Two Human Prostate Tumor Models

To determine the in vivo effect of the overexpression of ΔH2 relaxin on prostate tumor cells PC3-Luc xenograft tumors were generated in NOD/SCID mice. Tumors were palpable by week 3, and thereafter tumor volume was determined by caliper measurement. Compared with PC3-Luc-H2/eGFP tumors over-expressing wild-type H2 relaxin, PC3-Luc-ΔH2/eGFP tumors exhibited a significantly smaller tumor volume starting at week 4 (0.61-fold; P=0.043) until termination of the study at week 11 (0.56-fold; P=0.018; FIG. 3A). With one exception at week 6, there were no significant differences in tumor volume between PC3-Luc-H2/eGFP and PC3-Luc-eGFP tumors throughout the study period.

This experiment also determined how long-term overexpression of H2 relaxin affects PC3-Luc tumor cell metastasis. Previously, $3.5\times10^6$ tumor cells per NOD/SCID mouse were delivered and tumor growth was monitored for up to 6 weeks with no evidence of metastasis observed (Silvertown, J. D., Ng, J., Sato, T., Summerlee, A. J., Medin, J. A. 2006. H2 relaxl; overexpression increases in vivo prostate xenograft tumor growth and angiogenesis. *Iift J Cancer.* 118:62-73). Presently, $2\times10^6$ cells were injected to allow prolonged relaxin expression and animal monitoring before tumor size reached terminal endpoints, thereby permitting an extended opportunity to observe metastasis. At weeks 9 and 11, all animals were imaged for luciferase expression to a) confirm general size of tumors as measured with calipers, and b) assist in identifying PC3-Luc metastatic events. FIG. 3B illustrates the location, size and cell density proportionate to level of luciferase expression (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118:62-73) of a tumor from representative animals from each PC3-Luc tumor group. This method of bioluminescence imaging (BLI) confirms that PC3-Luc-H2/eGFP and PC3-Luc-eGFP tumors have significantly larger tumor volumes at weeks 9 and 11 compared to PC3-Luc-ΔH2/eGFP tumors. Upon termination of the study at week 11, a complete blinded autopsy was conducted on each animal. Putative metastatic tumors were harvested and imaged to confirm that the tissue originated from the PC3-Luc tumors (FIG. 3C). In animals bearing PC3 Luc-H2/eGFP tumors, 3 of 7 mice were found to have metastatic events compared to only 1 of 7 and 1 of 6 mice in the PC3-Luc-ΔH2/eGFP and PC3-Luc-eGFP groups, respectively. Tumors were also harvested and imaged for eGFP expression with a fluorescent stereomicroscope before tumor tissue processing (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118: 62-73). Imaged tumors were confirmed to fluoresce from eGFP expression, due to the bicistronic format of the LV expression cassette. This indicates that H2 and ΔH2 relaxins were being expressed because they are located upstream to the IRES element (FIG. 1C).

To demonstrate whether ΔH2 relaxin overexpression had similar effects on other human prostate cancer models, LNCaP (androgen-independent) xenograft tumors were grown in NOD/SCID mice. From pilot studies, it was observed that tumors grown from this cell line, whether implanted in male or female NOD/SCID mice, never grew large enough for caliper measurement. LNCaP-ΔH2/eGFP tumors (59.2±3.5 mg) exhibited a significantly lighter tumor weight after 14 weeks in vivo compared to LNCaP-eGFP (72.9±5.2 mg; P~0.05) and LNCaPH2/eGFP (73.9±8.7 mg) tumors (Table 1). Similar to the PC3-Luc prostate tumor xenograft model, mice bearing H2 relaxin-overexpressing tumors exhibited greater metastatic incidences (n=3/8) compared to mice bearing LNCaP-ΔH2/eGFP (n 1/8) and LNCaP-eGFP (n 1/8) tumors.

TABLE 1

Tumor weights and metastasis incidence in NOD/SCID mice bearing LV-engineered LNCaP prostate xenograft tumors. LV-infected LNCaP cells (6 × 10$^6$) were implanted s.c in the dorsal right flank of NOD/SCID mice (n = 8 per group). Tumors were harvested and weighed 14 weeks after implantation and animals were autopsied and examined for evidence of metastases.

| | Tumor Weight (mg) | No. of Mice Presenting Metastatic Events |
|---|---|---|
| LNCaP-eGFP (n = 8) | 72.9 ± 5.2 | 1/8 (12.5%) |
| LNCaP-H2/eGFP (n = 8) | 73.9 ± 8.7 | 3/8 (37.5%) |
| LNCaP-ΔH2/eGFP (n = 8) | 59.2 ± 3.5* | 1/8 (12.5%) |

*P = 0.05 compared to LNCaP-H2/EGFP group.

Example 3

PC3-Luc Xenograft Tumors Retain Relaxin Expression after 11 Weeks

To confirm after 11 weeks in vivo that PC3-Luc-H2/eGFP and PC3-Luc-ΔH2/eGFP tumors were still secreting H2 and ΔH2 relaxins, respectively, ~75 mg of tissue from one randomly selected tumor from each group upon harvest was minced and collagenase-treated to grow as cell cultures. Day four CM from these PC3-Luc tumor cell cultures were subjected to an H2 relaxin ELISA and cells were processed for flow cytometry analysis (Table 2). The PC3-Luc-H2/eGFP sample contained 340±60 pg/mL H2 relaxin compared to 155±15 and 86±15 pg/mL H2 relaxin for PC3-Luc AH2/eGFP and PC3-Luc-eGFP CM samples, respectively. Despite PC3 Luc-H2/eGFP cell cultures being only 13% eGFP positive compared to approximately 85% at implantation, these cultures still contained more H2 relaxin compared to PC3-Luc ΔH2/eGFP (87% eGFP positive) and PC3-Luc-eGFP (86% eGFP positive) CM samples. Under a fluorescent microscope, these partially eGFP positive tumors exhibited a marbling pattern of varying green fluorescence (data not shown). We have previously shown that is due to the variation in eGFP intensities within the PC3-Luc infected pools (Silvertown, J. D., Ng, J., Sato, T., Summerlee, A. J., Medin, J. A. 2006. H2 relaxl; overexpression increases in vivo prostate xenograft tumor growth and angiogenesis. Iift J. Cancer. 118: 62-73). Differences in the percentage of eGFP positive cells from the PC3-Luc tumor cell cultures (i.e. before implantation and after tumor harvesting) is likely due to the random sampling of excised tumor and not due to the loss (or silencing) of LV-engineered transgene expression. Therefore, these data verify that PC3-Luc tumors were secreting levels of H2/ΔH2 relaxins for the duration of the experiment.

TABLE 2

PC3-Luc prostate tumor xenografts retain transgene expression after 11 weeks in vivo. PC3-Luc tumors (n = 1 per group) were harvested, minced, collagenase-treated, and cultured for 4 days. Cells were harvested for FACS analysis to measure eGFP expression and conditioned medium was collected to measure H2 relaxin by ELISA from PC3-Luc cells re-cultured in vitro.

| | % Positive eGFP | | H2 Relaxin (pg/mL) | |
|---|---|---|---|---|
| | Before Implantation | After Tumor Harvesting | Before Implantation | After Tumor Harvesting |
| LNCaP-eGFP | 85% | 86% | 48.9 ± 10 | 86 ± 15 |
| LNCaP-H2/eGFP | 85% | 13% | 1135 ± 69 | 340 ± 60 |
| LNCaP-ΔH2/eGFP | 85% | 87% | 253 ± 95 | 155 ± 15 |

Example 4

Mutated H2 Relaxin (AH2) Modulates Physiological Parameters In Vivo

In addition to measuring tumor growth, downstream pathways affected by H2 relaxin overexpression were investigated. The regulation of MMPs by relaxin in tumors (Silvertown, J. D., Ng, J., Sato, T., Summerlee, A. J., Medin, J. A. 2006. H2 relaxl; overexpression increases in vivo prostate xenograft tumor growth and angiogenesis. Iift J. Cancer. 118: 62-73) and in other systems (9) has been previously reported. Gelatin zymography was employed as a technique LV detect the presence of gelatinase A (MMP-2) and gelatinase B (MMP-9) activity in tumor cell lysates. Cell lysates prepared from PC3-Luc-eGFP tumors consistently exhibited significantly greater levels of MMP-9 activity (FIG. 4A) compared to other samples. PC3-Luc ΔH2/eGFP cell lysate samples appeared to exhibit intermediate levels of MMP-9 enzyme activity suggesting that ΔH2 relaxin is affecting PC3-Luc signaling pathways responsible for MMP-9 expression.

As an indicator of H2 relaxins role in the present tumors, evidence of intra-tumoral and extra-tumoral vascularization was measured (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73) by immunohistochemical staining of ECs with anti-mouse CD31 (PECAM-1). Brown-stained ECs and vessels, clustered in dense regions ('hot spots'), were manually counted from four fields within four sections from each tumor (FIG. 4B). Extra-tumoral microvessel density (MVD) was determined to be significantly greater (~1.5-fold; P<0.01) in PC3-Luc-H2/eGFP tumors (28.7±4.6) compared to PC3-Luc-eGFP tumors (18.8±2.6). Although there was no significant difference in intra-tumoral MVD in PC3-Luc-H2/eGFP tumors (1 8.g12.7' compared to PC3-Luc-eGFP tumors (14.2±2.3) a trend was observed where the PC3-H2/eGFP, PC3-Luc-AH2/eGFP and PC3-Luc-eGFP tumors had the greatest, intermediate and least number of MVD counts, respectively.

The influence that H2 and ΔH2 relaxins have on PC3-Luc tumor xenografts may be achieved at the level of signaling pathways between tumor and host. To determine if the influence of H2 and ΔH2 relaxins can occur in the absence of in vivo signals, an in vitro soft agarose colony assay was employed. PC3-Luc colony spheres were grown, suspended in a three-dimensional agar matrix complete with all cell culture components. After 5 weeks in culture, PC3-Luc colony spheres were counted, measured and imaged (FIG. 4C). No apparent size differences were observed between the PC3-H2/eGFP, PC3-Luc-ΔH2/eGFP and PC3-Luc-eGFP colony spheres (data not shown) suggesting that the differences in tumor growth in NOD/SCID mice are likely due to angiogenic or other in vivo signaling pathways which are absent from this assay.

To determine whether H2 and ΔH2 relaxins secreted from the PC3-Luc tumor xenografts elicited a systemic physiological response, plasma osmolality was measured from the animals at the termination of the study (FIG. 4D). Plasma osmolality readings obtained from PC3-H2/eGFP, PC3-Luc-eGFP and PC3-Luc-ΔH2/eGFP animals averaged 330±4.6 339±F5 and 342±4.6 mmol/L, respectively. PC3-Luc-ΔH2/eGFP animals exhibited significantly greater levels of plasma osmolality (12 mmol/L; P=0.04) compared to PC3-Luc-H2/eGFP animals and only slightly greater levels compared to PC3-Luc-eGFP samples. Differences of MVD and MVA between treatment groups suggest that ΔH2 relaxin may be affecting pathways of angiogenesis. PC3-Luc-H2/eGFP tumors had about two-fold greater MVA compared to PC3-Luc-ΔH2/eGFP and PC3-Luc-eGFP tumors (FIG. 4E). This suggests that H2 relaxin has a role in prostate tumor growth not just by enhancing vascularization. Overexpression of ΔH2 relaxin in the tumor microenvironment may inhibit endogenous H2 relaxin progrowth signals to tumor cells or tumor-infiltrated ECs. These findings demonstrate that locally-expressed AH2 relaxin has systemic effects.

Example 5

Intratumoral Delivery of LV-zIH2/eGFP Suppresses Tumor Growth

Figure 5:
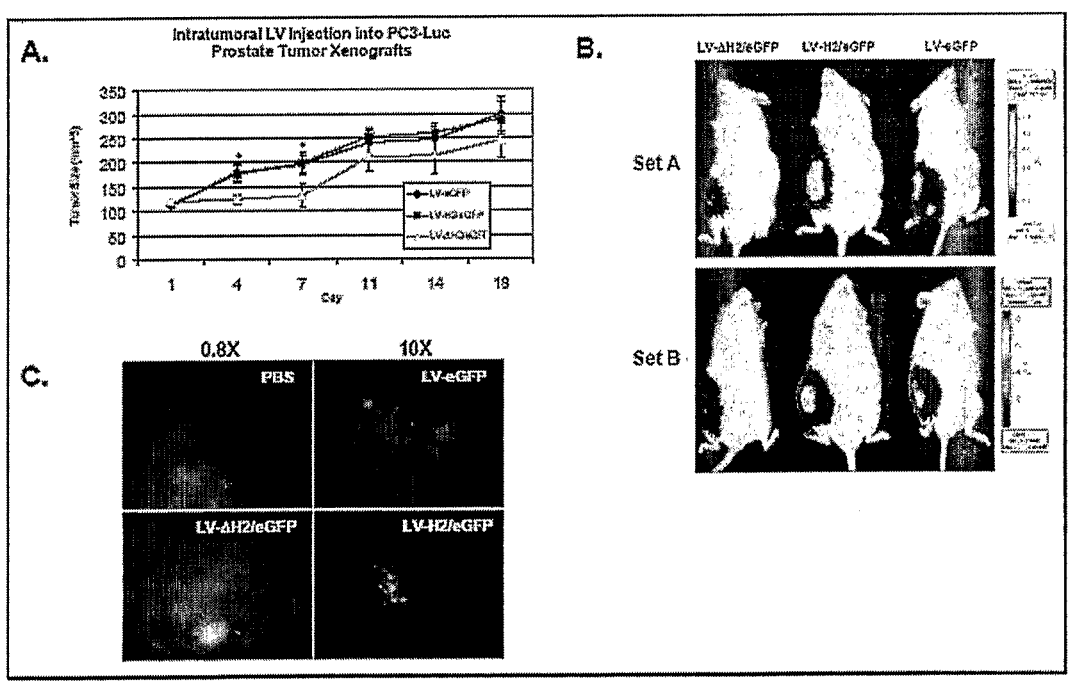
FIGS. 5A-C show intratumoral LV delivery to PC3-Luc prostate tumor xenografts. Male NOD/SCID mice were implanted with $3\times10^6$ PC3-Luc cells and xenografts were grown until they reached approximately 1 cm³. Tumors were measured by calipers and injected every 3 or 4 days with 20 μL ($4\times10^6$ infectious units) of the concentrated LV suspension (n=5 per group). 5A) shows the PC3-Luc tumor growth curve. 5B) shows BLI of two sets of representative animals from each group at day 18. 5C) Representative harvested tumors were imaged at 0.8× and 10× magnifications for eGFP expression using a fluorescent stereomicroscope.

To demonstrate the therapeutic utility of ΔH2 relaxin, LVs engineering the expression of either H2 relaxin and eGFP, ΔH2 relaxin and eGFP, or eGFP alone were delivered intratumorally to mice over an 18-day period. Tumors were first grown to 1 cm$^3$, and then injected every 3-4 days with 20 μL of concentrated LV suspensions. During the first 7 days, LV-ΔH2/eGFP-injected tumors exhibited a significant suppression in growth (131±25.3 mm$^3$) compared to LV-H2/eGFP (199±20.3 mm$^3$ P~0.04) and LV-eGFP-injected (195±20.7 mm$^3$ P=0.05) tumors (FIG. 5A). Thereafter, LV-AH2/eGFP~injected tumors displayed moderately suppressed tumor volume compared to tumors receiving LV-H2/eGFP or LV-eGFP. At the end of the study, animals were imaged (as above) to measure tumor size, density and location. FIG. 5B shows two sets of representative animals from each group, illustrating the apparent tumor suppression observed in mice bearing LV-ΔH2/eGFP-injected tumors compared to LV-H2/eGFP and LV-eGFP-injected tumors. Upon autopsy, a single metastatic event among all animals was found in one LV-eGFP-treated mouse (data not shown). To confirm that the tumor cells were LV-transduced (i.e. positive for eGFP expression), tumors were harvested and imaged under a fluorescent stereomicroscope (FIG. 5C). Compared to PBS injected controls, LV-treated mice had regions positive for eGFP expression within the tumor (0.8× magnification). At 10× magnification, clusters of transduced cells present at the LV injection sites on the tumor can be distinguished.

Example 6

Primary Human Prostate Cancer Tissue Secretes H2 Relaxin

Figure 6:
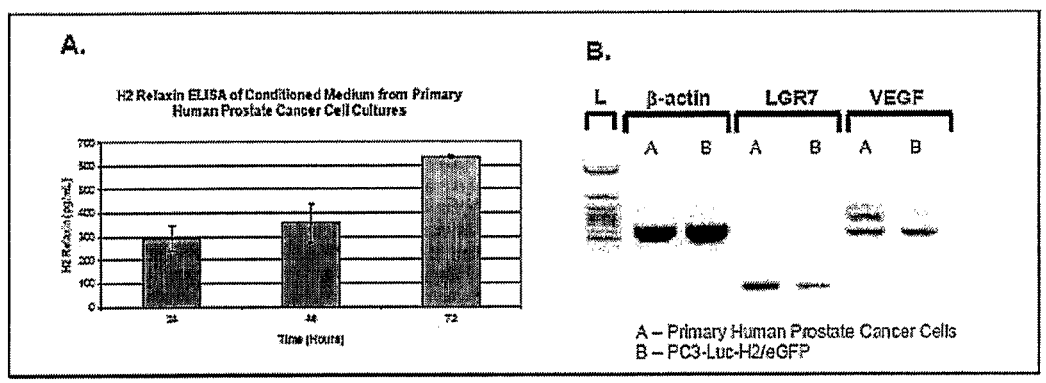
FIGS. 6A-B show the characterization of H2 relaxin expression from primary human prostate cancer cell cultures. 6A) shows H2 relaxin is secreted from primary cell cultures over a three-day period, as detected by an H2 relaxin ELISA. Experiments were performed in triplicate and repeated three times from the same sample. 6B) RT-PCR from PC3-Luc-H2/eGFP and human primary prostate cancer biopsy cell cultures. Transcripts for LGR7 (244 bp) and VEGF isoforms are present in greater levels in human primary prostate cancer cells compared to the PC-3 human prostate cancer cell line, establishing a potential clinical relevance for the role of relaxin in prostate cancer. A β-actin band at the expected size of 540 bp was also observed confirming fidelity of the sample preparations. L: 50 bp ladder (NEB).
Figure 7:
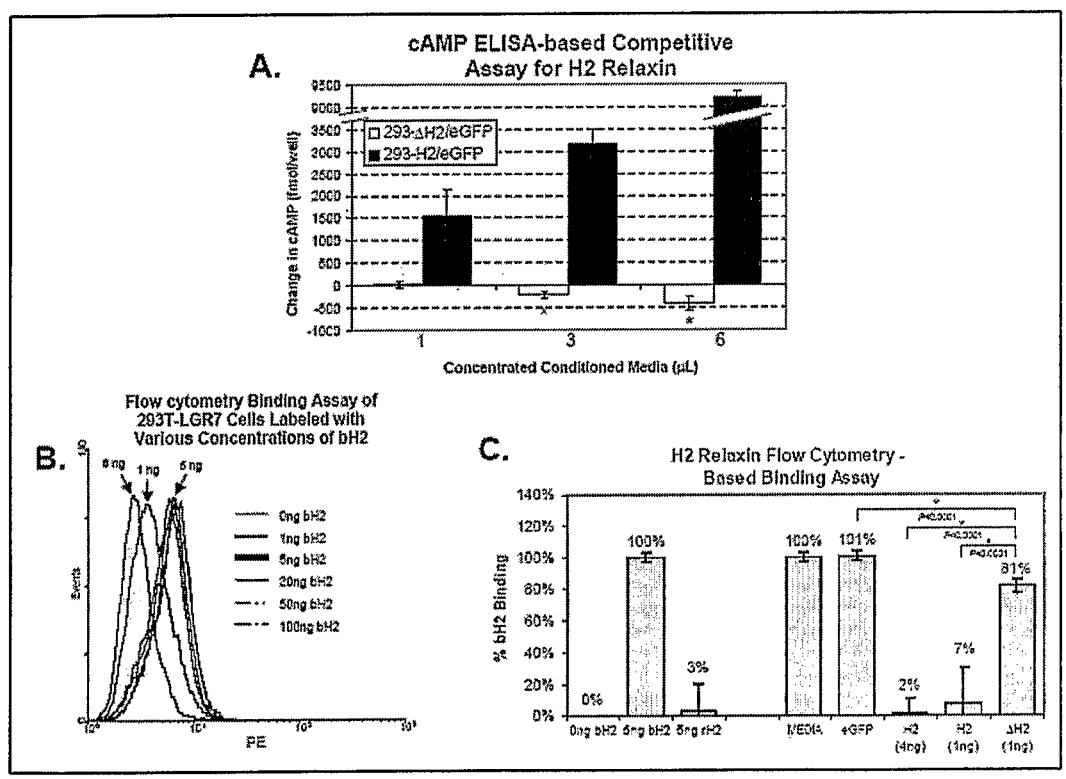
FIGS. 7A-C show mutated H2 relaxin (ΔH2) exhibits antagonistic properties and receptor binding capacity. 7A) A THP-1 cAMP competitive assay was developed to measure the antagonistic properties of ΔH2. THP-1 cells were coincubated with 0.4 ng rH2 relaxin and varying volumes (1, 3, 6 μL) of concentrated LV-infected 293T conditioned medium containing WT H2 relaxin, ΔH2 relaxin, or eGFP control. At each sample volume, values were normalized against 293T-eGFP samples. Increasing amounts of 293T-ΔH2/eGFP CM had a consistent and significant effect of reducing cAMP levels compared to 293T-eGFP control samples, indicated at baseline "0". Increasing amounts of 293-H2/eGFP concentrated conditioned medium resulted in a consistent and significant stimulation of cAMP levels compared to 293T-eGFP control samples. Experiments were performed in triplicate and repeated three time. *$P<0.05$. 7B) Overlay histogram of 293T-LGR7 cells subjected to varying quantities of bH2 relaxin. 293T-LGR7 ($5\times10^5$ cells per sample) were incubated with 0, 5, 20, 50, or 100 ng of bH2 relaxin in PBS supplemented with 1% FCS for 15 min at RT, washed, and then stained with streptavidin-PE (1 mg/mL). 7C) Results of a flow cytometry-based binding assay using 293T-LGR7 cells demonstrates that WT H2 relaxin and mutated ΔH2 relaxin exhibit high and low receptor affinity. Unconcentrated conditioned media containing WT H2 relaxin (1 and 4 ng/mL), ΔH2 relaxin (1 ng/mL) or control medium were collected from LV-infected 293T clonal cell cultures, and applied to 293T-LGR7 cells before receptor binding was competed with bH2 (5 ng).
Figure 8:
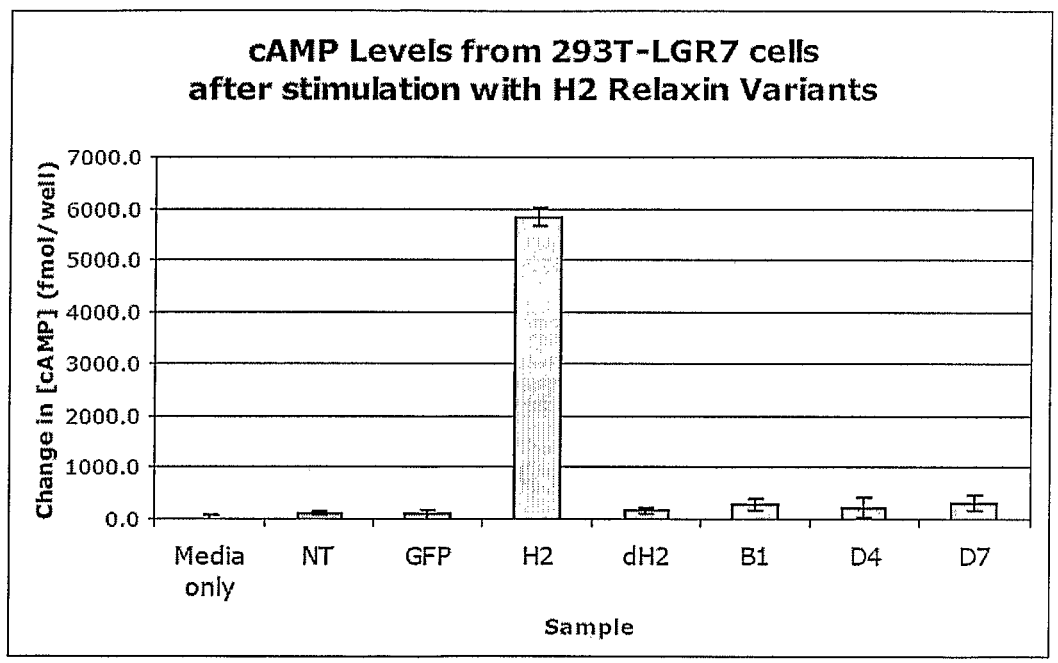
FIG. 8 shows cAMP levels from 293T-LGR7 cells after stimulation with H2 relaxin antagonists in conditioned medium from engineered 293 cell cultures. All of these H2 relaxin antagonists exhibited no cAMP stimulation, the levels were similar to controls and not elevated.

It was previously shown that PC-3 cells secrete H2 relaxin, express VEGF and the LGR7 relaxin receptor, and exhibit sensitivity to H2 relaxin binding (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73). We determined that primary human prostate tissue secretes H2 relaxin. H2 relaxin was detected by ELISA in the CM from primary human prostate cancer cell cultures, which accumulated in a time-dependent manner over three days, measuring up to 636±10 pg/mL (FIG. 6A). RT-PCR analysis of primary cell samples indicated that both LGR7 and VEGF mRNA transcripts are present at greater levels compared to transcripts found in control PC3-Luc-H2/eGFP cell line samples (FIG. 6B). An additional VEGF isoform was detected in the primary prostate cancer cell samples, which was not found in the PC3-Luc samples.

Example 7

Cell Lines and Culture Conditions

Cell lines were obtained from the ATCC (Rockville, Md., USA). The human embryonic kidney cell line, 293T, was cultured in DMEM. The human prostate cancer cell line, PC-3, was cultured in Nutrient Mixture F12 Ham Medium supplemented with 2 mM L-glutamine. The human prostate cancer cell line, LNCaP, was cultured in RPMI 1640 medium. The human monocytic cell line, THP-1, was grown in RPMI 1640 medium with 2 mM L-glutamine, adjusted to contain 1.5 g/L sodium bicarbonate, 4.5 g/L glucose, 10 mM HEPES and 1.0 mM sodium pyruvate and supplemented with 0.05 mM 2-mercaptoethanol. All culture media (Sigma; Oakville, ON, Canada) were supplemented with 10% Fetal Calf Serum (FCS, Gemini Bio-Products, Woodland, Calif., USA), 100 U/mL penicillin and 10 pg/mL streptomycin. Cells were cultured at 37° C. in a humidified atmosphere with 5% $CO_2$.

Example 8

Engineering of Mutant H2 Relaxin (∆H2) and Construction of Lentiviral Vectors The H2 relaxin cDNA present in a CMV-H2-IRES-eGFP expression cassette (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73) 20) was mutated using the QuikChange Site-Directed Mutagenesis Kit (Stratagene, La Jolla, Calif., USA). The nucleotides encoding the two arginine residues (R) of the classic receptor binding motif were replaced with nucleotides that encode lysine residues (FIG. 1). This cDNA was denoted ∆H2. LVs were constructed to engineer expression of the CMV-H2-IRES-eGFP, CMV-∆H2-IRES eGFP and CMV-IRES-eGFP cassettes in the pHR LV backbone (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73). LV virions were produced by a transient triple-transfection method using 293T monolayers. Briefly, 293T celL were seeded in 15 cm diameter plates at a density of ~11×10$^6$ cells in DMEM supplemented with 10% FCS. Following a 24 h incubation, cells were transfected using a calcium phosphate method (27) with 32 µg of one of three gene transfer vectors (pHR-cPPT-CMV-H2-IRES-eGFP-WPRE, pHR-cPPT-CMV ∆H2-IRES-eGFP-WPRE or pHR-cPPT-CMV-IRES-eGFP-WPRE), 16.25 µg of packaging vector (pCMV∆R8.91) and 7 µg of the VSV-g envelope vector (pMDG). After 48 h, viral supernatants were harvested, filtered with a 0.45 µm unit (Nalgene; Rochester, N.Y., USA), concentrated at 28,000 rpm for 1.5 h by ultracentrifugation, and re suspended in tissue-grade water (Sigma) giving a 300-fold concentrated vector stock. Viral supernatants were titered on naive 293T cells by serial dilutions and analyzed 72 h later by flow cytometry (FACSCalibur, BO; San Jose, Calif., USA) for eGFP expression. Concentrated LV titers ranged from 1×10$^8$-5×10$^8$ productive 293T infectious units/mL.

Example 9

Generation of Engineered PC-3 and 293T Cell Lines

The human prostate cancer cell line, PC-3, was engineered and clonally-selected to express luciferase (PC3-Luc; 7). For this study, the PC3-Luc and 293T cell lines were transduced with viral supernatants (LV-H2/eGFP, LV-∆H2/eGFP or LV-eGFP) for 24 h, followed by a change in culture medium. LV-infected PC3-Luc cell cultures were termed PC3-Luc-H2/eGFP, PC3-Luc-∆H2/eGFP and PC3-Luc-eGFP, respectively. To generate relatively uniform populations, the upper 10% of PC3-Luc eGFP-expressing cells were sorted using a MoFlo cytoometer [Cytomation Inc., Princess Margaret Hospital (PMH), Toronto, Canada]. After expansion, PC3-Luc cell lines were re-analyzed by FACSCalibur and Cell Quest software (BD; San Diego, Calif., USA) for eGFP expression. LV-infected 293T cell lines were also analyzed for eGFP expression as above and populations were selected that were approximately 50% and 90% for eGFP-positive expression. Cell cultures were termed 293T-H2/eGFP (50%), 293T-∆H2/eGFP (50%), 293T-∆H2/eGFP (90%) and 293T-eGFP (50%). All plots were gated on live cells after 7-AAD (Sigma) labeling of dead cells.

Example 10

Characterization of PC3-Luc-H2/eGFP Cells

H2 relaxin expression from the transduced PC3-Luc and 293T cells lines was confirmed by ELISA analysis. Transduced PC3-Luc and 293T cell lines were seeded in serum-free media at density of 3.5×10$^6$ and 5×10$^6$ cells in 10 cm diameter plates. Samples were harvested at the specified time, lyophilized, and resuspended in $\frac{1}{10}$th or $\frac{1}{15}^{th}$ the original volume. To determine the amount of H2 relaxin peptide released into the cell culture medium, a recombinant human H2 relaxin-specific direct sandwich ELISA was performed as previously described (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73; Parsell, D. A., Mak, J. Y., Amento, E P., Unemori, E. N. 1996. Relaxin binds to and elicits a response from cells of the human monocytic cell line, THP-1. *J Biol. Chem.* 271:27936-41).

To confirm the biological activity of the H2 and ∆H2 relaxins, the cAMP Biotrak E1A System was employed (Amersham Biosciences) as described before (Parsell, D. A., Mak, J. Y., Amento, E P., Unemori, E. N. 1996. Relaxin binds to and elicits a response from cells of the human monocytic cell line, THP-1. *J Biol Chem.* 271:27936-41; Silvertown, J. D., Geddes, B. J., Summerlee, A. J. 2003. Adenovirus mediated expression of human prorelaxin promotes the invasive potential of canine mammary cancer cells. Endocrinology. 144: 3683-91). For measuring bioactivity from CM, 40 µL from each concentrated CM sample was added to THP-1 cells. For measuring cAMP levels directly from the LV-infected PC3-Luc cells, 1×10$^5$ cells were seeded in a 96-well plate and equilibrated for 2 h before cAMP was measured as described (Parsell, D. A., Mak, J. Y., Amento, E P., Unemori, E. N. 1996. Relaxin binds to and elicits a response from cells of the human monocytic cell line, THP-1. *J Biol Chem.* 271:27936-41; Silvertown, J. D., Geddes, B. J., Summerlee, A. J. 2003. Adenovirus-mediated expression of human prorelaxin promotes the invasive potential of canine mammary cancer cells. Endocrinology. 144:3683-91). The THP-1 cAMP assay was also adapted for an H2 relaxin competitive assay. All steps remained consistent with previous assays with the exception that THP-1 cells were co incubated with 0.4 ng rH2 (BAS Medical, Inc, San Francisco, Calif.) and varying volumes (1, 3, 6, 9 pL) of concentrated CM from LV-infected 293T cell cultures.

Example 11

Cell Proliferation Assays

Two assays were employed to measure cell proliferation. PC3-Luc-eGFP, PC3-Luc-H2/eGFP and PC-3-Luc-∆H2/eGFP cells were plated in triplicate at 1×10$^3$, 3×10$^3$ and 8×10$^3$ cells per well in a 96-well dish. For the thymidine incorporation assay, cells were incubated in F12 medium containing 0.5% FCS for 24 hours to induce cell cycle synchronization. At 24, 48, and 72 h after original plating, 100 µl F12 medium containing 1 µCi/mL [methyl-$^3$H]thymidine (Amersham Biosciences Inc., Quebec, Canada) was added and cells incubated at 37° C. and 5% CO$_2$ for an additional 24 h. Cells were washed once in PBS, harvested using 0.25% trypsin with EDTA (Invitrogen, Burlington, ON, Canada) and collected using a PHD cell harvester (Cambridge Technology Inc., Watertown, Mass.) onto glass filter paper (Brandel, Inc., Gaithersburg, Md.). The filter paper was dried 1 h at 60° C.

and analyzed using a liquid scintillation counter (LS 1801, Beckman Coulter, Mississauga, ON, Canada). Results are presented as counts/minute. Cell proliferation was also measured at 24, 48, and 72 h using the CellTiter 96® Aqueous One Solution Cell Proliferation Assay reagent (Promega) according to the manufacturer's conditions.

Example 12

PC3-Luc Human Prostate Tumor Model in NOD/SCID Mice

Six-to-eight week old male NOD/SCID mice (The Jackson Laboratory; Bar Harbour, Me.) wore maintained at the Animal Resource Facility (PMH, Toronto, Canada) under an approved UHN protocol. Groups consisted of NOD/SCID mice injected with $2 \times 10^6$ PC3-Luc-H2/eGFP, PC3-Luc-ΔH2/eGFP, or PC3-Luc-eGFP cells suspended in 200 μL of Matrigel (BD; n=6 or 7 animals/group). Injections were performed s.c into the dorsal right flank of NOD/SCID mice. Tumors were measured weekly by calipers and tumor volume approximated (l×w×d), as described previously (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118:62-73). At weeks 9 and 11, animals underwent whole-body non-invasive BLI to examine PC3-Luc cell biodistribution (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118:62-73). After sacrificing animals, blinded autopsies were performed to examine for metastatic events. To confirm that the metastatic tissue was of PC3-Luc origin, tissue was placed in a 6-well dish, incubated in luciferin and imaged as described previously (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118:62-73). Tumors were harvested and examined for eGFP expression as previously described (Silvertown, J. D., Ng, J., Sato, T., Summerlee, A. J., Medin, J. A. 2006. H2 relaxl; overexpression increases in vivo prostate xenograft tumor growth and angiogenesis. Iift J Cancer. 118:62-73). Following imaging, tumors were subsequently separated into equal halves and randomly assigned. One half was sectioned, paraffin-embedded and stained with anti-mouse CD31 (PE-CAM-1) and the other half was homogenized in 1 mL of sterile PBS for collection of tumor cell lysates for analysis of gelatinase expression by gelatin zymography (see Silvertown J. D. et al, 2006 Int. J. Cancer, 118:62-73 for all methods). For plasma osmolality readings, approximately 100-200 μL of blood was collected in heparin (heparin sodium, 1000 USP units/mL; Hepalean) and sent for analysis (Animal Health Laboratory, Department of Pathobiology, University of Guelph).

Example 13

LNCaP Human Prostate Tumor Model in NOD/SCID Mice

LNCaP cells were transduced with LV supernatants (LV-H2-IRES-eGFP, LV-ΔH2-IRES-eGFP or LV-eGFP) to generate LV-infected LNCaP cell cultures, analogous to methods described for PC3-Luc cells. Cell lines (~85% eGFP positive) were termed LNCaP-H2/eGFP, LNCaPΔH2/eGFP and LNCaP-eGFP. H2 and ΔH2 relaxin expression and bioactivity were confirmed by employing the H2 relaxin ELISA and the THP-1 cAMP assay as described above. Groups consisted of five-week-old female NOD/SCID mice injected with $6 \times 10^6$ LNCaP-H2/eGFP, LNCaP-A1-12/eGFP and LNCaP-eGFP cells (n=8 animals/group) suspended in 200 μL of Matrigel (BD) into the dorsal right flank. After 14 weeks, blinded autopsies on mice were performed to examine for metastases. Tumors were harvested, imaged and weighed as described above.

Example 14

Collagenase Digestion of PC3-Luc Tumors for eGFP Expression Analysis

Approximately 75 mg of tumor tissue was excised and minced using scalpels from one randomly selected mouse per group at the time of sacrifice. Tumors were digested for 1.5 h in HBSS (Cambrex Bio Science Walkersville Inc.) with 1.5 mg/mL Collagenase B (Roche Diagnostics Corp., Indianapolis, Ind.) and 105 U/mL DNaseI (Invitrogen). Cell clumps were mechanically separated with a pipette, passed through a 30 μm cell strainer and cultured in PC3 culture medium. Cells were analyzed by flow cytometry (as above) to verify eGFP expression.

Example 15

PC3-Luc Soft Agarose Colony Assay

Powdered F12 Nutrient mixture (Gibco) was prepared as a sterile 2× complete medium buffered with sodium bicarbonate to pH 7.67. Six-well culture dishes were coated with 1.5 mL/well of 1:1 mixture of 0.8% sterile low melting agarose (NuSieve GTG agarose; BioWhittaker Molecular Applications, ME, USA) mixed with 2×F12 medium (supplemented with 20% FCS, 200 U/mL penicillin; 20 μg/mL streptomycin) and stored at 4° C. to solidify. Then 1.5 mL of varying dilutions of PC3-Luc-H2/eGFP, PC3-Luc-ΔH2/eGFP or PC3-Luc-eGFP cells (ranging from 100-1,000 cells/mL) suspended in F12/0.4% agarose solution were applied in triplicate to the coated 6-well plates. Wells were replenished with fresh F12/0.4% agarose solution every 3-4 days for 5 weeks. Colony spheres were counted, measured and imaged using a Nikon TE200 inverted microscope mounted with a Hamamatsu ORCA 100 camera, and analyzed with SimplePCI version 3.1 software (Compix Inc.)

Example 16

Intratumoral Delivery of Lentiviral Vectors to PC3-Luc Tumors

NOD/SCID male mice (n=15) were injected in the dorsal right flank with $3 \times 10^6$ PC3-Luc cells suspended in 200 μL of Matrigel (BD). When tumors reached approximately 1 cm$^3$, animals were divided into three groups to equally distribute age and weight of the mice. Every 3 or 4 days for 18 days, tumors were injected in four random sites with 5 μL of concentrated LV suspension (LV-H2/eGFP, LV ΔH2/eGFP, LV-eGFP) per site using a 25 μL Hamilton microsyringe (total=~$4 \times 10^6$ infectious units). Tumors were measured on the day of each intratumoral LV delivery by calipers and tumor volume approximated. At day 18, animals underwent whole body non-invasive BLI and a complete autopsy to examine for PC3-Luc cell biodistribution (Silvertown, J. D., Ng, J., Sato, T., Summerlee, A. J., Medin, J. A. 2006. H2 relaxl; overexpression increases in vivo prostate xenograft tumor growth and angiogenesis. *Iift J Cancer.* 118:62-73). After euthanizing animals, tumors were harvested and examined for eGFP expression as previously described (Silvertown, J. D., Ng, I, Sato, T., Summerlee, A. J., Medin, J. A. 2006. H2 relaxl; overexpression increases in vivo prostate xenograft tumor growth and angiogenesis. *Iift J Cancer.* 118:62-73).

Example 17

Primary Human Prostate Cancer Cell Culture

Primary prostate cancer tissue was obtained from a patient undergoing radical prostatectomy (Gleason score 8 tumor) using a protocol approved by the University Health Network (UHN) Research Ethics Board. Tissue was finely minced using scalpels and digested for 18 h at 37° C. in 10 mL of PrEGM™ prostate epithelial cell medium BulletKit® (Cambrex Bio Science Walkersville, Inc., Walkersville, Md.) and 100 U/mL collagenase I (Sigma). Cell clumps were mechanically separated with a pipette and centrifuged for 20 s at 250 g. Cells were washed in PBS and resuspended in 5 mL of PrEGM and plated on 10 cm diameter tissue culture dishes coated in 20% Vitrogen-100® purified bovine collagen I (Cohesion Technologies, Palo Alto, Calif.) and 80% 0.013N hydrochloric acid. Cells were cultured at 37° C. in a humidified atmosphere with 5% $CO_2$ for 2 weeks. RNA was extracted from cells (Silvertown, J. D., Ng, J., Sato, T., Summerlee, A. J., Medin, J. A. 2006. H2 relaxl; overexpression increases in vivo prostate xenograft tumor growth and angiogenesis. *Iift J. Cancer.* 118:62-73) and RT-PCR was performed for LGR-7 and VEGF using the method previously described (Silvertown, J. D., Ng, J., Sato, T., Summerlee, A. J., Medin, J. A. 2006. H2 relaxl; overexpression increases in vivo prostate xenograft tumor growth and angiogenesis. *Iift J Cancer.* 118:62-73). Cells were seeded in 6-well dishes to be 80% confluent by the next day. CM was collected from primary prostate cancer cells after 24, 48 and 72 h incubations in 1 mL PrEGM. This media was centrifuged for 5 mm at 8000 rpm and 4° C. to remove cell debris before storage at −20° C. The H2 ELISA was carried out as previously described (Parsell, D. A., Mak, J. Y., Amento, E P., Unemori, E. N. 1996. Relaxin binds to and elicits a response from cells of the human monocytic cell line, THP-1. *J Biol. Chem.* 271:27936-41; Silvertown, J. D., Geddes, B. J., Summerlee, A. J. 2003. Adenovirus-mediated expression of human prorelaxin promotes the invasive potential of canine mammary cancer cells. *Endocrinology.* 144:3683-91).

Example 18

Flow Cytometry-Based Relaxin Binding Assay

To optimize collection of recombinant ΔH2 peptide for this assay, single-cell clones of LV-infected 293T cell cultures were isolated. Clones were confirmed by flow cytometry measuring eGFP fluorescence and selected based on highest expression. 293T-eGFP#3, 293TΔH2/eGFP#6, 293T-H2/eGFP#3 cell cultures were seeded in 15-cam plates in complete medium overnight, refreshed with Dulbecco's Modified Eagle Medium (DMEM) medium containing 2% FCS after 24 h, and incubated for an additional 48 h. At this point, CM were collected for assays. H2 relaxin levels in unconcentrated CM from 293T-eGFP#3, 293TΔH2/eGFP#6, 293T-H2/eGFP#3 cell cultures were approximated by the H2 ELISA to be 0, 1, and 4 ng/mL (data not shown).

293T-LGR7 cells were collected, washed with PBS supplemented with 1% FCS (PBS-1%), and resuspended at $1.67 \times 10^7$ cells/mL. For each sample, 30 μl ($0.5 \times 10^6$ cells/mL) were added per 5 mL polystyrene round-bottom Falcon tube (Becton Dickinson Labware, Franklin Lakes, N.J., USA). Control samples contained 50 μL of either PBS-1% containing 5 ng of rH2 or 50 μL of PBS-1% alone. Each control sample was then supplemented with 20 μL of 0.25 ng/μL bH2 in PBS-1% or PBS-1% alone, giving a total volume of 100 μL. Samples were incubated for 15 min at RT. Each sample was then supplemented with either 70 μL of either media alone (DMEM, 2% FBS), or CM from 4-day cultures of LV-transduced 293T clones and incubated for 5 min at RT. Cells were collected by centrifugation at 350 g for 3 min, resuspended in 100 μl of additional media or CM as above, and incubated for 5 min at RT. Following two washes, 20 μL of 0.25 ng/μL bH2 in PBS-1% was added for a total volume of 100 μL and incubated for 15 mins at RT. Samples were washed with 500 μL of PBS-1% and cells were collected by centrifugation at 400 g for 3 min and resuspended in 100 μL of 1 μg/mL of streptavidin-phycoerithrin (PE) reagent (eBioscience, San Diego, Calif., USA) in PBS-1% and incubated in the dark for 15 min at 4° C. Cells were washed twice with 500 μL of PBA-1% and analyzed on a FACSCalibur flow cytometer) BDBiosciences, Franklin Lakes, N. J., USA).

To determine whether mouse relaxins can bind to human LGR7, relative affinity of mouse relaxin and mouse relaxin-3 hormone were also measured in parallel. CM containing LV-engineered recombinant mouse relaxin and mouse relaxin-3 were prepared as described previously. The flow cytometry-based binding assay for mouse relaxins were performed as above with the following modification: 293T-LGR7 cells were preincubated with CM (diluted 2-fold, and 20-fold) for 5 min at RT before addition of 10 ng of bH2. As above, the addition of controls containing bH2, rH2 and CM containing human H2 relaxin were also included.

Example 19

Preparation of biotin-X-X-rhH2 (bH2)

Human recombinant relaxin was labeled with 6-(biotinamidocaproylamido) caproic acid N-hydroxysuccinimide ester (Biotin-X-X-NHS, MW 567.70; Sigma-Aldrich, Saint Louis, Mo., USA). Briefly, 5 μg of rH2 was added at a 1:20 M ratio with Biotin-X-X-NHS (reconstituted in dimethylformamide at 25 mg/mL in a total volume of 250 μl of PBS (pH 7.3) on ice for 1.5 h. The reaction was quenched b the addition of 1 μl of 1M Tris-HCl (pH 88.0). The product was then dialyzed in 500 mL of PBS at RT overnight to remove uncoupled biotinylation reagent in a 3500 Da MW cut-off dialysis chamber (Elutatube Dialysis Kit; Fermemtas, Burlington, ON, Canada). The final product was aliquoted and stored at −20° C. until use. To confirm that bH2 did not differ in biological activity from rH2, 0.4 ng of each was subjected to the THP-1 cAMP assay as described above. Bioactivities of bH2 and rH2 remained virtually the same with demonstrated cAMP levels of 316±7.5 and 307±9.2 fmol/well, respectively (data not shown).

Statistical Analysis

Differences between two treatment groups were statistically analyzed using a two-tailed, independent samples t test. Differences among three or more groups were analyzed using a one-way ANOVA test. To account for multiple comparisons testing of the tumor volume, a Bonferroni t test within each time point was performed to make adjustment to the P values. Plasma osmolality data were analyzed using a median two-sample test (SAS). Error bars indicate the se, and significance is indicated by an asterisk when P_0.05. Statistical analyses were performed under consultation with the Clinical Studies Resource Centre, UHN (Toronto, Canada).

The invention claimed is:

1. A method for treating cancer in a reproductive tissue of a subject, the method comprising administering to said subject in need thereof, a therapeutically effective amount of a H2 relaxin antagonist comprising (i) an A-chain and (ii) a B-chain or a homolog or analog of the B-chain, wherein the B-chain comprises an amino acid modification at position 13, 17, 20 or a combination thereof of the amino acid sequence DSWMEEVIKLCGRELVRAQIAICGMSTWS, wherein the first residue (D) is at position 1 and the last residue (S) is at position 29, and wherein the B-chain homolog or analog comprises an amino acid modification at a position equivalent to position 13, 17, 20 or a combination thereof.

2. The method of claim 1, wherein said modification comprises a substitution, deletion or an addition at position 13, 17, 20 or a combination thereof.

3. The method of claim 2, wherein said substitution comprises lysine for the arginine residues at positions 13 and 17 of the B-chain.

4. The method of claim 1, wherein said antagonist is selected from the group consisting of dH2, A1, A2, B1, B2, B3, C1, C2, D10, D2, D3, D4, D5, D6, D7, D8 and D9.

5. The method of claim 1, wherein said antagonist is administered in a route selected from the group consisting of infusion, injection, oral delivery, subcutaneously and intratumorally.

6. The method of claim 1, wherein said cancer is prostate cancer.

7. The method of claim 1, wherein said method further comprises the administration of one or more cancer therapeutic agents.

8. A method for the treatment of a tumor in a reproductive tissue expressing a relaxin receptor in a subject, the method comprising administering an effective amount of a H2 relaxin antagonist for a period of time sufficient to reduce the size of the tumor,
wherein the H2 relaxin antagonist comprises (I) an A-chain and (ii) a B-chain or a homolog or analog of the B-chain, wherein the B-chain comprises an amino acid modification at position 13, 17, 20 or a combination thereof of the amino acid sequence DSWMEEVIKLCGRELVRAQIAICGMSTWS, wherein the first residue (D) is at position 1 and the last residue (S) is at position 29, and wherein the B-chain homolog or analog comprises an amino acid modification at a position equivalent to position 13, 17, 20 or a combination thereof.

9. A method for the treatment of prostate cancer in a subject, said method comprising administering a therapeutically effective amount of a H2 relaxin antagonist comprising (i) an A-chain and (ii) a B-chain or a homolog or analog of the B-chain, wherein the B-chain comprises an amino acid modification at position 13, 17, 20 or a combination thereof of the amino acid sequence DSWMEEVIKLCGRELVRAQIAICGMSTWS, wherein the first residue (D) is at position 1 and the last residue (S) is at position 29, and wherein the B-chain homolog or analog comprises an amino acid modification at a position equivalent to position 13, 17, 20 or a combination thereof,
and
optionally administering one or more other cancer therapies to said subject for a time and under conditions effective to inhibit growth of the prostate cancer, or
optionally treating said subject with surgery or radiation therapy to remove the prostate cancer or inhibit growth of the prostate cancer.

10. The method of claim 1, wherein the subject is a human.

11. The method of claim 1, wherein the reproductive tissue is prostate, testes, ovarian, cervical or endometrial tissue.

12. A method for treating breast cancer in a subject, the method comprising administering to said subject in need thereof, a therapeutically effective amount of a H2 relaxin antagonist comprising (i) an A-chain and (ii) a B-chain or a homolog or analog of the B-chain, wherein the B-chain comprises an amino acid modification at position 13, 17, 20 or a combination thereof of the amino acid sequence DSWMEEVIKLCGRELVRAQIAICGMSTWS, wherein the first residue (D) is at position 1 and the last residue (8) is at position 29, and wherein the B-chain homolog or analog comprises an amino acid modification at a position equivalent to position 13, 17, 20 or a combination thereof.

13. The method of claim 12, wherein said modification comprises a substitution, deletion or an addition at position 13, 17, 20 or a combination thereof.

14. The method of claim 13, wherein said substitution comprises lysine for the arginine residues at positions 13 and 17 of the B-chain.

15. The method of claim 12, wherein said antagonist is selected from the group consisting of dH2, A1, A2, B1, B2, B3, C1, C2, D10, D2, D3, D4, D5, D6, D7, D8 and D9.

16. The method of claim 12, wherein said antagonist is administered in a route selected from the group consisting of infusion, injection, oral delivery, subcutaneously and intratumorally.

17. The method of claim 12, wherein said method further comprises the administration of one or more cancer therapeutic agents.

18. A method for the treatment of a breast tumor expressing a relaxin receptor in a subject, the method comprising administering an effective amount of a H2 relaxin antagonist for a period of time sufficient to reduce the size of the tumor, wherein the H2 relaxin antagonist comprises (i) an A-chain and (ii) a B-chain or a homolog or analog of the B-chain, wherein the B-chain comprises an amino acid modification at position 13, 17, 20 or a combination thereof of the amino acid sequence DSWMEEVIKLCGRELVRAQIAICGMSTWS, wherein the first residue (D) is at position 1 and the last residue (S) is at position 29, and wherein the B-chain homolog or analog comprises an amino acid modification at a position equivalent to position 13, 17, 20 or a combination thereof.

19. The method of claim 12, wherein the subject is a human.

20. A method for treating cancer in a reproductive tissue comprising administering to a subject in need thereof a gene delivery vehicle, wherein the gene delivery vehicle comprises a polynucleotide that encodes an H2 relaxin antagonist peptide,
wherein the polynucleotide expresses the H2 relaxin antagonist peptide in an amount which is effective to treat said cancer, and
wherein said H2 relaxin antagonist peptide comprises (i) an A-chain and (ii) a B-chain or a homolog or analog of the B-chain, wherein the B-chain comprises an amino acid modification at position 13, 17, 20 or a combination thereof of the amino acid sequence DSWMEEVIKLCGRELVRAQIAICGMSTWS, wherein the first residue (aspartic acid) is at position 1 and the last residue (serine) is at position 29, and wherein the B-chain homolog or analog comprises an amino acid modification at a position equivalent to position 13, 17, 20 or a combination thereof.

21. The method of claim 20, wherein said modification comprises a substitution, deletion or an addition at position 13, 17, 20 or a combination thereof.

22. The method of claim 21, wherein said substitution comprises lysine for the arginine residues at positions 13 and 17 of the B-chain.

23. The method of claim 20, wherein said antagonist is selected from the group consisting of dH2, A1, A2, B1, B2, B3, C1, C2, D10, D2, D3, D4, D5, D6, D7, D8 and D9.

24. The method of claim 20, wherein said gene delivery vehicle is administered in a route selected from the group consisting of infusion, injection, oral delivery, subcutaneously and intra-tumorally.

25. The method of claim 20, wherein said cancer is prostate cancer.

26. The method of claim 20, wherein said method further comprises the administration of one or more cancer therapeutic agents.

27. The method of claim 20, wherein the subject is a human.

28. The method of claim 20, wherein the reproductive tissue is prostate, testes, ovarian, cervical or endometrial tissue.

29. A method for treating breast cancer in a subject, the method comprising administering to said subject in need thereof a gene delivery vehicle, wherein the gene delivery vehicle comprises a polynucleotide that encodes an H2 relaxin antagonist peptide,
wherein the polynucleotide expresses the H2 relaxin antagonist peptide in an amount which is effective to treat said breast cancer, and
wherein said H2 relaxin antagonist peptide comprises (i) an A-chain and (ii) a B-chain or a homolog or analog of the B-chain, wherein the B-chain comprises an amino acid modification at position 13, 17, 20 or a combination thereof of the amino acid sequence DSWMEEVIKL-CGRELVRAQIAICGMSTWS, wherein the first residue (aspartic acid) is at position 1 and the last residue (serine) is at position 29, and wherein the B-chain homolog or analog comprises an amino acid modification at a position equivalent to position 13, 17, 20 or a combination thereof.

30. The method of claim 29, wherein said modification comprises a substitution, deletion or an addition at position 13, 17, 20 or a combination thereof.

31. The method of claim 30, wherein said substitution comprises lysine for the arginine residues at positions 13 and 17 of the B-chain.

32. The method of claim 29, wherein said antagonist is selected from the group consisting of dH2, A1, A2, B1, B2, B3, C1, C2, D10, D2, D3, D4, D5, D6, D7, D8 and D9.

33. The method of claim 29, wherein said gene delivery vehicle is administered in a route selected from the group consisting of infusion, injection, oral delivery, subcutaneously and intra-tumorally.

34. The method of claim 29, wherein said method further comprises the administration of one or more cancer therapeutic agents.

35. The method of claim 29, wherein the subject is a human.

\* \* \* \* \*

UNITED STATES PATENT AND TRADEMARK OFFICE
CERTIFICATE OF CORRECTION

PATENT NO. : 8,445,635 B2  
APPLICATION NO. : 12/664824  
DATED : May 21, 2013  
INVENTOR(S) : Jeffrey A. Medin et al.

Page 1 of 1

It is certified that error appears in the above-identified patent and that said Letters Patent is hereby corrected as shown below:

In the Claims

In claim 1 at column 31, line 11, "DSWMEEV1KLCGRELVRAQ1A1CGMSTWS" should read "DSWMEEVIKLCGRELVRAQIAICGMSTWS";

In claim 8 at column 31, line 39, "(1)" should read "(i)";

In claim 8 at column 31, lines 43-44, "DSWMEEV1KLCGRELVRAQ1A1CGMSTWS" should read "DSWMEEVIKLCGRELVRAQIAICGMSTWS";

In claim 9 at column 31, lines 55-56, "DSWMEEV1KLCGRELVRAQ1A1CGMSTWS" should read "DSWMEEVIKLCGRELVRAQIAICGMSTWS";

In claim 12 at column 32, lines 11-12, "DSWMEEV1KLCGRELVRAQ1A1CGMSTWS" should read "DSWMEEVIKLCGRELVRAQIAICGMSTWS";

In claim 12 at column 32, line 13, "(8)" should read "(S)";

In claim 18 at column 32, line 41, "DSWMEEV1KLCGRELVRAQ1A1CGMSTWS" should read "DSWMEEVIKLCGRELVRAQIAICGMSTWS";

In claim 20 at column 32, lines 61-62, "DSWMEEV1KLCGRELVRAQ1A1CGMSTWS" should read "DSWMEEVIKLCGRELVRAQIAICGMSTWS"; and In claim 29 at column 34, lines 5-6, "DSWMEEV1KLCGRELVRAQ1A1CGMSTWS" should read "DSWMEEVIKLCGRELVRAQIAICGMSTWS".

Signed and Sealed this  
Twenty-ninth Day of July, 2014

Michelle K. Lee  
*Deputy Director of the United States Patent and Trademark Office*